US012569483B2

(12) United States Patent
Niculescu

(10) Patent No.: US 12,569,483 B2
(45) Date of Patent: Mar. 10, 2026

(54) METHODS FOR OBJECTIVE ASSESSMENT OF MEMORY, EARLY DETECTION OF RISK FOR ALZHEIMER'S DISEASE, MATCHING INDIVIDUALS WITH TREATMENTS, MONITORING RESPONSE TO TREATMENT, AND NEW METHODS OF USE FOR DRUGS

(71) Applicants: Indiana University Research and Technology Corporation, Bloomington, IN (US); The United States Government as Represented by the Department of Veterans Affairs, Washington, DC (US)

(72) Inventor: Alexander Bogdan Niculescu, Indianapolis, IN (US)

(73) Assignees: Indiana University Research and Technology Corporation, Bloomington, IN (US); The United States Government as Represented by the Department of Veterans Affairs, Washington, DC (US)

( * ) Notice: Subject to any disclaimer, the term of this patent is extended or adjusted under 35 U.S.C. 154(b) by 962 days.

(21) Appl. No.: 17/613,000

(22) PCT Filed: May 22, 2020

(86) PCT No.: PCT/US2020/034358
§ 371 (c)(1),
(2) Date: Nov. 19, 2021

(87) PCT Pub. No.: WO2020/237203
PCT Pub. Date: Nov. 26, 2020

(65) Prior Publication Data
US 2022/0211700 A1 Jul. 7, 2022

Related U.S. Application Data

(60) Provisional application No. 62/852,081, filed on May 23, 2019.

(51) Int. Cl.
*A61K 31/496* (2006.01)
*A61K 31/202* (2006.01)
*A61K 33/00* (2006.01)
*A61K 45/06* (2006.01)
*G16B 25/10* (2019.01)

(52) U.S. Cl.
CPC .......... *A61K 31/496* (2013.01); *A61K 31/202* (2013.01); *A61K 33/00* (2013.01); *A61K 45/06* (2013.01); *G16B 25/10* (2019.02)

(58) Field of Classification Search
CPC .... A61K 31/496; A61K 31/202; A61K 33/00; A61K 45/06; G16B 25/10
See application file for complete search history.

(56) References Cited

U.S. PATENT DOCUMENTS

| | | | |
|---|---|---|---|
| 4,810,497 | A | 3/1989 | Horrobin |
| 9,102,679 | B2 | 8/2015 | Giovannini et al. |
| 2007/0049565 | A1 | 3/2007 | Gwag et al. |
| 2012/0283114 | A1 | 11/2012 | Cohen et al. |
| 2016/0230227 | A1 | 8/2016 | Sproul et al. |
| 2018/0024146 | A1 | 1/2018 | Khan et al. |

FOREIGN PATENT DOCUMENTS

| | | | | |
|---|---|---|---|---|
| EP | 0234733 | A1 | 9/1987 | |
| WO | 2012/096873 | A1 | 7/2012 | |
| WO | 2014/074942 | A1 | 5/2014 | |
| WO | WO-2016201299 | A1 * | 12/2016 | ............. A61P 25/00 |
| WO | 2018/119018 | A1 | 6/2018 | |

OTHER PUBLICATIONS

Le-Niculescu H. Discovery and validation of blood biomarkers for suicidality. Molecular Psychiatry 18: 1249-1264. (Year: 2013).*
Niculescu AB. Understanding and predicting suicidality using a combined genomic and clinical risk assessment approach. Molecular Psychiatry 20: 1266-1285. (Year: 2015).*
Levey DF. Towards understanding and predicting suicidality in women: biomarkers and clinical risk assessment. Molecular Psychiatry 21: 768-785. (Year: 2016).*
Kurian SM. Identification of blood biomarkers for psychosis using convergent functional genomics. Molecular Psychiatry 16: 37-58. (Year: 2011).*
Grünblatt E. Gene expression as peripheral biomarkers for sporadic Alzheimer's disease. Journal of Alzheimer's Disease 16: 627-634. (Year: 2009).*
Maes OC. Transcriptional profiling of Alzheimer blood mononuclear cells by microarray. Neurobiology of Aging 28: 1795-1809. (Year: 2007).*
International Search Report and Written Opinion, issued by the ISA/US, Commissioner for Patents, dated Oct. 14, 2020 for International Application No. PCT/US2020/034358; 10 pages.
International Preliminary Report on Patentability received for PCT Patent Application No. PCT/US2020/034358, mailed on Dec. 2, 2021, 8 pages.

(Continued)

*Primary Examiner* — Olivia M. Wise
*Assistant Examiner* — Robert J. Kallal
(74) *Attorney, Agent, or Firm* — Faegre Drinker Biddle & Reath LLP

(57) ABSTRACT

Disclosed are methods for assessing severity, determining future risk, matching with a drug treatment, and measuring response to treatment, for memory dysfunction, Alzheimer's disease, and cognitive decline. Also disclosed are new methods of use for drugs and natural compounds repurposed for use in improving memory, as well as for preventing and treating memory disorders, Alzheimer's disease and cognitive decline. All the above-mentioned methods are computer assisted methods analyzing the expression of panels of genes, clinical measures, and drug databases. A universal approach in everybody, as well as a personalized approaches by gender, and by diagnosis, are disclosed.

4 Claims, 7 Drawing Sheets

(56) References Cited

OTHER PUBLICATIONS

Invitation to Pay Additional Fees received for PCT Patent Application No. PCT/US2020/034358, mailed on Aug. 10, 2020, 2 pages.

Danthiir et al., "Omega-3 Polyunsaturated Fatty Acids, Apoe [4 Allele Status, and Cognitive Functioning in Community-dwelling Older Adults", Alzheimer's & Dementia, Elsevier, New York, NY, US, vol. 5, No. 4, Jul. 1, 2009, p. e21.

European Search Report for EP Patent Application No. 20809961.4 , Issued on Oct. 12, 2023, 20 pages.

Hanf et al., "Estimating associations between antidepressant use and incident mild cognitive impairment in older adults with depression", PLOS ONE, vol. 15, No. 1, Jan. 17, 2020, pp. e0227924.

Niculescu et al., "Blood biomarkers for memory: toward early detection of risk for Alzheimer disease, pharmacogenomics, and repurposed drugs", Molecular Psychiatry, Nature Publishing Group UK, London, vol. 25, No. 8, Dec. 2, 2019, pp. 1651-1672.

Supplementary European Search Report for EP Patent Application No. 20809961.4, Issued on Jun. 1, 2023, 14 pages.

Zoladz et al., "Tianeptine: An Antidepressant with Memory-Protective Properties", Current Neuropharmacology, vol. 6, No. 4, Dec. 1, 2008, pp. 311-321.

Cacabelos et al., "Personalized Medicine of Alzheimer's Disease", Handbook of Pharmacogenomics and Stratified Medicine, vol. 27, No. 1, 2014, pp. 563-615.

* cited by examiner

Discovery Cohort
(Within-Subject Changes in Memory Retention )
(N=159)

Prioritization using Convergent
Functional Genomics

Independent Testing Cohort
State Low Memory Retention (N= 127)
Trait Future Positive Neuropsych Testing(N=56)

FIG 3A

Predictions for State – Low Memory Retention State

| AUCs | All | | Gender | | | | Personalized (Gender/Dx) | | | | | | | | | | | | | | | | | | |
|------|-----|-----|-----|-----|-----|-----|-----|-----|-----|-----|-----|-----|-----|-----|-----|-----|-----|-----|-----|-----|-----|-----|-----|-----|-----|
| ≥ 0.7 | 0 | 3 | 0 | 2 | 1 | 4 | 1 | 13 | 25 | 16 | 1 | 16 | 3 | NA | 1 | NA | 0 | 4 | 0 | 5 | 2 | 6 | 1 | 17 | 3 | 6 |
| ≥ 0.6 | 0 | 10 | 1 | 9 | 2 | 4 | 4 | 13 | 25 | 16 | 3 | 16 | 3 | NA | 1 | NA | 2 | 4 | 0 | 5 | 4 | 6 | 3 | 17 | 3 | 6 |
| ≥ 0.5 | 3 | 10 | 4 | 9 | 2 | 4 | 4 | 13 | 25 | 16 | 3 | 16 | 3 | NA | 1 | NA | 2 | 4 | 0 | 5 | 4 | 6 | 3 | 17 | 3 | 6 |

Predictions for Trait – Future Positive Neuropsychological Testing

| Odds Ratio | All | | Gender | | Personalized (Gender/Dx) | | | | | |
|---|---|---|---|---|---|---|---|---|---|---|
| ≥ 2.0 | 1 | 3 | 8 | 5 | 3 | NA | 5 | 5 | 2 | 3 |
| ≥ 1.5 | 5 | 3 | 10 | 5 | 3 | NA | 6 | 5 | 3 | 3 |
| ≥ 1 | 5 | 3 | 10 | 5 | 3 | NA | 6 | 5 | 3 | 3 |

METHODS FOR OBJECTIVE ASSESSMENT OF MEMORY, EARLY DETECTION OF RISK FOR ALZHEIMER'S DISEASE, MATCHING INDIVIDUALS WITH TREATMENTS, MONITORING RESPONSE TO TREATMENT, AND NEW METHODS OF USE FOR DRUGS

CROSS-REFERENCE TO RELATED APPLICATION

This application is a national phase filing of International Application No. PCT/US2020/034358, filed May 22, 2020, which claims priority to U.S. Provisional Application No. 62/852,081 filed on May 23, 2019, the disclosures of which are incorporated herein by reference in their entirety.

STATEMENT OF GOVERNMENT SUPPORT

This invention was made with government support under OD007363 awarded by the National Institutes of Health and CX000139 merit award by the Veterans Administration. The government may have rights in the invention.

BACKGROUND

Alzheimer's disease is a clear and present danger to older adults, and has a profound socio-economic impact. Existing therapies are limited in efficacy. Early identification of subjects at risk may open the door to preventive approaches. Short-term memory dysfunction is a key early feature of Alzheimer's disease. Psychiatric patients may be at higher risk for memory dysfunction and subsequent Alzheimer's disease due to the negative effects of stress and depression on the brain.

Existing drugs have potential utility in other diseases and disorders. Biomarkers can serve as companion diagnostics for clinical trials for the development of new medications and also for repurposing existing drugs for other diseases and disorders.

Accordingly, methods are needed for early identification of memory dysfunction and Alzheimer's disease. Additionally, methods are needed for identifying and repurposing existing drugs and natural compounds for use as treatments of other disorders and diseases.

SUMMARY

The present disclosure is generally directed at methods for assessing memory dysfunction and early identification/prediction of risk for future memory dysfunction, Alzheimer's disease and cognitive decline, using computer assisted methods that derive scores based on biomarker data, in some instances blood biomarker data. Further, the present disclosure relates to methods for matching individuals with drugs to reduce the risk of and mitigate memory dysfunction, Alzheimer's disease and cognitive decline, and methods for monitoring response to treatment. Finally, the invention relates to new methods of use for candidate drugs and natural compounds repurposed for treating memory dysfunction, Alzheimer's disease and cognitive decline. All the above-mentioned methods may include computer-assisted methods that generate scores based on analyses of the expression of panels of genes, clinical measures, and drug databases. A universal approach in everybody, as well as a personalized approach by gender, and by diagnosis, are disclosed.

In one aspect, the present disclosure is directed to a method for identifying a biomarker for Alzheimer's disease, the method comprising: obtaining a first biological sample from a subject and administering a first memory test to the subject; obtaining a second biological sample from the subject and administering a second memory test to the subject; identifying a first cohort of subjects by identifying subjects having about 20% change in a memory retention characteristic as determined by a difference between the first memory test and the second memory test; identifying candidate biomarkers in the first cohort by identifying biomarkers having a change in expression.

In one aspect, the present disclosure is directed to a method to reduce the risk of and mitigate memory dysfunction, Alzheimer's disease, and cognitive decline in a subject in need thereof, the method comprising administering a therapy to the subject, the therapy being selected from the group consisting of one or more compounds from Tables 5A1-A5, and 5B1-B5, and 5C1-C2.

In one aspect, the present disclosure is directed to a computer-implemented method for assessing a low memory state in a subject, and for assessing risk of future Alzheimer Disease and cognitive decline in a subject, the method comprising: computing a score based on RNA level, protein level, DNA methylation, a single nucleotide polymorphism, a panel of at least one biomarker in one of Table 2, Table 4A and Table 4B, and combinations thereof in a sample obtained from a subject; computing a score based on a reference expression level of the panel of biomarkers; and identifying a difference between the score in the sample obtained from the subject and the score in the reference sample, wherein the difference in the score in the sample obtained from the subject and the score in the reference sample indicates a risk for a low memory state in the subject.

In other aspects, the present disclosure is directed to a method for assessing and mitigating memory dysfunction, Alzheimer's disease, and cognitive decline in a subject in need thereof, comprising determining an expression level of a panel of biomarkers listed in Table 2, Table 4, or Table 5 in a sample, wherein the expression level of the biomarkers in the sample is different relative to a reference expression level, identifying the subject currently having or at risk of having in the future memory dysfunction, Alzheimer's disease, and cognitive decline based on a biomarker panel score relative to a biomarker panel score of a reference; and administering to the subject a therapy being selected based on the score from the group consisting of one or more compounds from Tables 5A1-A5, and 5B1-B5, and 5C1-C2.

In some aspects, of the disclosed methods, the therapy is lithium, an antidepressant, pioglitazone, sulfadimidine, SB-203580, mesalazine, metamizole, levonorgestrel, meglumine, lymecycline, rimexolone, ketanserin, quipazine, cisapride, proparacaine, tenoxicam, bexarotene, an omega-3 fatty acid, salsolidine, ginkgolide A, icariin, docosahexaenoic acid, or combinations thereof.

In some aspects, the sample comprises a peripheral tissue, blood, saliva, cerebrospinal fluid (CSF), serum, urine, or stool.

In other aspects, the present disclosure is directed to a composition comprising one or more compounds from Tables 5A1-A5, and 5B1-B5, and 5C1-C2 for use in a method for treating memory dysfunction, Alzheimer's disease, and cognitive decline.

In some aspects, the compound comprises lithium, an antidepressant, pioglitazone, sulfadimidine, SB-203580, mesalazine, metamizole, levonorgestrel, meglumine, lymecycline, rimexolone, ketanserin, quipazine, cisapride, proparacaine, tenoxicam, bexarotene, an omega-3 fatty acid, salsolidine, ginkgolide A, icariin, docosahexaenoic acid, or combinations thereof. In some aspects, the compound comprises one or more of the compounds from Tables 5A1-A5, and 5B1-B5, and 5C1-C2.

DESCRIPTION OF THE DRAWINGS

FIG. 1A depicts the cohorts used in study, depicting flow of discovery, prioritization, and testing of biomarkers. FIG. 1B depicts the differential gene expression in the discovery cohort-number of genes identified with differential expression (DE) and absent-present (AP) methods with an internal score of 2 and above. In FIG. 1C, the pyramid on the left depicts the number of discovery step probesets, identified based on their score for tracking memory, with a maximum of internal points of 6 (33% (2 pt), 50% (4 pt) and 80% (6 pt)), and the pyramid on the right depicts prioritization with CFG for prior evidence of involvement in AD.

FIGS. 3A and 3B are graphs depicting the best single biomarkers for predictors of state (low memory retention state) (FIG. 3A) and trait (future neuropsychosis) (FIG. 3B). Bold—top CFG scoring biomarkers on the list (CFG≥12, n=21 probe sets). Bar graph shows best predictive biomarkers in each group. *Nominally significant p<0.05. Table underneath the figures displays the actual number of biomarkers for each group whose ROC AUC p-values (FIG. 3A) and Cox Regression Odds Ratio p-values (FIG. 3B) are at least nominally significant. Some female diagnostic groups were not shown in the graph as they did not have subjects to be tested or any significant biomarkers. Cross-sectional was based on levels at one visit. Longitudinal was based on levels at multiple visits (integrates levels at most recent visit, maximum levels, slope into most recent visit, and maximum slope). Dividing lines represent the cutoffs for a test performing at chance levels (white), and at the same level as the best biomarkers for all subjects in cross-sectional (gray) and longitudinal (black) based predictions. All biomarkers performed better than chance. Biomarkers performed better when personalized by gender and diagnosis.

DETAILED DESCRIPTION

Figure 1A:
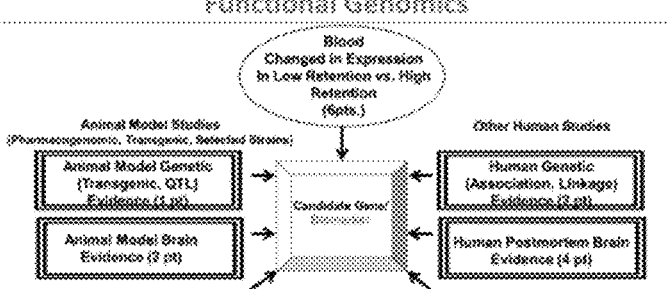
FIGS. 1A-1C are illustrations depicting the methods described in the present disclosure.

Disclosed are methods for identifying biomarkers for memory dysfunction and early identification of Alzheimer's disease. Also disclosed are methods using biomarker expression levels for identifying and treating one or more populations or subpopulations for reducing risk of and mitigating memory dysfunction, Alzheimer's disease, and cognitive decline. Further, the present disclosure relates to methods for identifying candidate drugs and natural compounds repurposed for treating memory dysfunction, Alzheimer's disease and cognitive decline. The methods are useful for early detection of Alzheimer's disease in subjects and identifying existing drugs and natural compounds that can be repurposed for treating subjects for memory dysfunction, Alzheimer's disease and cognitive decline.

In one aspect, the present disclosure is directed to a method for identifying a one or more biomarker(s) for Alzheimer's disease, the method comprising: obtaining a first biological sample from a subject and administering a first memory test to the subject; obtaining a second biological sample from the subject and administering a second memory test to the subject; identifying a first cohort of subjects by identifying subjects having about 20% change in a memory retention characteristic as determined by a difference between the first memory test and the second memory test; identifying candidate biomarker(s) in the first cohort by identifying biomarkers having a change in expression.

The method can further include prioritizing the candidate biomarkers by identifying candidate biomarkers known to be associated with Alzheimer's disease.

A suitable memory test is Hopkins Verbal Learning Test-Revised (HVLT-R). Suitable subjects include those having a psychiatric disorder. Suitable subjects can be male subjects and female subjects.

As used herein, "sample" or "biological sample" refers to the sample from which biomarkers are measured. In some embodiments, the sample is blood. In some embodiments, the sample can be saliva, cerebrospinal fluid (CSF), serum, urine, stool, and/or another bodily fluid. In some embodiments, the sample is a peripheral tissue.

As used herein, "expression level of a biomarker" refers to the process by which a gene product is synthesized from a gene encoding the biomarker as known by those skilled in the art. The gene product can be, for example, RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, enzyme linked immunosorbent assay (ELISA), and combinations thereof. In some embodiments, the biomarker is a polymorphic biomarker profile. In some embodiments, the polymorphic biomarker profile includes one or more single nucleotide polymorphisms (SNPs), one or more restriction fragment length polymorphisms (RFLPs), one or more short tandem repeats (STRs), one or more variable number of tandem repeats (VNTRs), one or more hypervariable regions, one or more minisatellites, one or more dinucleotide repeats, one or more trinucleotide repeats, one or more tetranucleotide repeats, one or more simple sequence repeats, or one or more insertion elements. In some embodiments, the methods further include establishing a profile of biomarkers.

As used herein, "a reference expression level of a biomarker" refers to the expression level of a biomarker established for a subject with no known memory dysfunction, Alzheimer's disease and cognitive decline, expression level of a biomarker in a normal/healthy subject with no known memory dysfunction, Alzheimer's disease and cognitive decline as determined by one skilled in the art using established methods as described herein, and/or a known expression level of a biomarker obtained from literature. The reference expression level of the biomarker can further refer to the expression level of the biomarker established for a high risk subject for memory dysfunction, Alzheimer's disease and cognitive decline, including a population of high risk subjects. The reference expression level of the biomarker can also refer to the expression level of the biomarker established for a low risk memory dysfunction, Alzheimer's disease and cognitive decline subject, including a population of low risk subjects. The reference expression level of the biomarker can also refer to the expression level of the biomarker established for any combination of subjects such as a subject with no known memory dysfunction, Alzheimer's disease and cognitive decline, expression level of the biomarker in a normal/healthy subject with no known memory dysfunction, Alzheimer's disease and cognitive decline, expression level of the biomarker for a subject who has no memory dysfunction, Alzheimer's disease and cognitive decline at the time the sample is obtained from the subject, but who later exhibits memory dysfunction, Alzheimer's disease and cognitive decline. For example, depending on the biomarker(s) selected, the difference in the expression level of the biomarker(s) can indicate an increased (greater) risk that a subject will develop symptoms consistent with memory dysfunction, Alzheimer's disease and cognitive decline. Conversely, depending on the biomarker(s) selected, the difference in the expression level of the biomarker(s) can indicate a decreased (lower) risk that a subject will develop symptoms with or memory dysfunction, Alzheimer's disease and cognitive decline.

In some embodiments, the methods can further include genotyping the subject. The genotyping can be performed by methods such as sequencing, nucleic acid array and PCR. The nucleic acid can be double-stranded DNA, single-stranded DNA, single-stranded DNA hairpins, DNA/RNA hybrids, RNA, RNA hairpins and cDNA. The presence or absence of the one or more nucleic acids can be determined by sequencing, nucleic acid array and PCR. Suitable nucleic acid arrays include DNA arrays such as, for example polymorphism arrays. Suitable polymorphism arrays include SNP arrays, for example.

In one aspect, the present disclosure is directed to a method for identifying a subject suspected of having Alzheimer's disease, the method comprising: obtaining a first biological sample from a subject; obtaining a second biological sample from the subject; and identifying the subject by identifying a change in expression of at least one of RAB7A, NPC2, TGFB1, GAP43, ARSB, PER1, GUSB, MAPT, FCGR1A, UBE2L3, NKTR, RHEB, PTGS2, RGS10, ITPKB, KIDINS220, GSK3B, SERTAD3, APOE, UBE2I, FOXO3, THRA, IGF1, NPTX2, GSTM3, BACE1, PSEN1, GFAP, TREM2, NOCT, CEP350, PPP2R2B, NRP2, CTSS, VEGFA, and combinations thereof.

The method can further include administering a memory test to the subject when the first biological sample is obtained from the subject and administering the memory test to the subject when the second biological sample is obtained from the subject; and determining a change in a memory retention characteristic as determined by a difference between the first memory test and the second memory test. Suitably, the memory test is Hopkins Verbal Learning Test-Revised (HVLT-R). The HVLT-R can be used to determine a 'Low Memory Retention', which as used herein, can also be called 'Low Memory State' or 'Low Memory Retention state' or 'Memory Retention measure.' Suitably, the subject can have about 20% change in a memory retention characteristic as determined by a difference between the first memory test and the second memory test.

Suitable subjects include those having a psychiatric disorder. Suitable subjects can be male subjects and female subjects.

Suitable subjects include subjects over 21 years old.

In one aspect, the present disclosure is directed to a method of prophylactically treating a subject for Alzheimer's Disease, the method comprising: obtaining a first biological sample from a subject; obtaining a second biological sample from the subject; and identifying a change in expression of at least one of RAB7A, NPC2, TGFB1, GAP43, ARSB, PER1, GUSB, MAPT, FCGR1A, UBE2L3, NKTR, RHEB, PTGS2, RGS10, ITPKB, KIDINS220, GSK3B, SERTAD3, APOE, UBE2I, FOXO3, THRA, IGF1, NPTX2, GSTM3, BACE1, PSEN1, GFAP, TREM2, NOCT, CEP350, PPP2R2B, NRP2, CTSS, VEGFA, and combinations thereof; identifying a difference between the expression level of the at least one of RAB7A, NPC2, TGFB1, GAP43, ARSB, PER1, GUSB, MAPT, FCGR1A, UBE2L3, NKTR, RHEB, PTGS2, RGS10, ITPKB, KIDINS220, GSK3B, SERTAD3, APOE, UBE2I, FOXO3, THRA, IGF1, NPTX2, GSTM3, BACE1, PSEN1, GFAP, TREM2, NOCT, CEP350, PPP2R2B, NRP2, CTSS, VEGFA, and combinations thereof, and a reference expression level of at least one of RAB7A, NPC2, TGFB1, GAP43, ARSB, PER1, GUSB, MAPT, FCGR1A, UBE2L3, NKTR, RHEB, PTGS2, RGS10, ITPKB, KIDINS220, GSK3B, SERTAD3, APOE, UBE2I, FOXO3, THRA, IGF1, NPTX2, GSTM3, BACE1, PSEN1, GFAP, TREM2, NOCT, CEP350, PPP2R2B, NRP2, CTSS, VEGFA, and combinations thereof; and administering a therapy to the subject.

Suitable therapies can include a drug, a natural compound, and combinations thereof. Suitable drugs can include lithium, an antidepressant, pioglitazone, levonorgestrel, and bexarotene, for example. Suitable natural compounds can include omega-3 fatty acid (e.g., docosahexaenoic acid), salsolidine, ginkgolide A, and icariin, for example.

In one aspect, the present disclosure is directed to a method for identifying a biomarker (e.g., a blood biomarker) for short-term memory dysfunction, the method comprising: obtaining a first biological sample from a subject and administering a first memory test to the subject; obtaining a second biological sample from the subject and administering a second memory test to the subject; identifying a first cohort of subjects by identifying subjects having about 20% change in a memory retention characteristic as determined by a difference between the first memory test and the second memory test; identifying candidate biomarkers in the first cohort by identifying biomarkers having a change in expression; and prioritizing the candidate biomarkers by identifying candidate biomarkers known to be associated with short-term memory.

The can further include prioritizing the candidate biomarkers by identifying candidate biomarkers known to be associated with short-term memory.

A suitable memory test is Hopkins Verbal Learning Test-Revised (HVLT-R).

Suitable subjects include those having a psychiatric disorder. Suitable subjects can be male subjects and female subjects.

In one aspect, the present disclosure is directed to a method for identifying a drug candidate for repurposing for use in treating Alzheimer's disease, the method comprising:

obtaining a first biological sample from a subject and administering a first memory test to the subject; obtaining a second biological sample from the subject and administering a second memory test to the subject; identifying a first cohort of subjects by identifying subjects having about 20% change in a memory retention characteristic as determined by a difference between the first memory test and the second memory test; identifying a candidate biomarker in the first cohort by identifying a biomarker having a change in expression; identifying a drug having an effect on the biomarker; and identifying the drug as a candidate for treating Alzheimer's disease.

Suitable drugs include those that reduce the activity of the biomarker. Other suitable drugs include those that increases the activity of the biomarker.

The biomarker is at least one of RAB7A, NPC2, TGFB1, GAP43, ARSB, PER1, GUSB, MAPT, FCGR1A, UBE2L3, NKTR, RHEB, PTGS2, RGS10, ITPKB, KIDINS220, GSK3B, SERTAD3, APOE, UBE2I, FOXO3, THRA, IGF1, NPTX2, GSTM3, BACE1, PSEN1, GFAP, TREM2, NOCT, CEP350, PPP2R2B, NRP2, CTSS, VEGFA, and combinations thereof.

In one aspect, the present disclosure is directed to a method for identifying a subject having or at risk for having cognitive decline, the method comprising: obtaining a first biological sample from a subject and administering a first memory test to the subject; obtaining a second biological sample from the subject and administering a second memory test to the subject; identifying a first cohort of subjects by identifying subjects having about 20% change in a memory retention characteristic as determined by a difference between the first memory test and the second memory test; identifying candidate biomarkers in the first cohort by identifying biomarkers having a change in expression; and prioritizing the candidate biomarkers by identifying candidate biomarkers known to be associated with cognitive decline.

The method can further include prioritizing the candidate biomarkers by identifying candidate biomarkers known to be associated with cognitive decline.

A suitable memory test is Hopkins Verbal Learning Test-Revised (HVLT-R).

In one embodiment, the subject also has a psychiatric disorder.

Suitable subjects are male subjects and female subjects.

The cognitive decline can be cognitive impairment dysfunction, mild cognitive impairment, and dementia.

In one aspect, the present disclosure is directed to a method of prophylactically treating a subject for cognitive decline, the method comprising: obtaining a first biological sample from a subject; obtaining a second biological sample from the subject; and identifying a change in expression of at least one of RAB7A, NPC2, TGFB1, GAP43, ARSB, PER1, GUSB, MAPT, FCGR1A, UBE2L3, NKTR, RHEB, PTGS2, RGS10, ITPKB, KIDINS220, GSK3B, SERTAD3, APOE, UBE2I, FOXO3, THRA, IGF1, NPTX2, GSTM3, BACE1, PSEN1, GFAP, TREM2, NOCT, CEP350, PPP2R2B, NRP2, CTSS, VEGFA, and combinations thereof; and administering a therapy to the subject.

Suitable therapies include drugs, natural compounds, and combinations thereof. In one embodiment, the subject can also have a psychiatric disorder. In s Suitable subjects are male subjects and female subjects.

The cognitive decline is cognitive impairment dysfunction, mild cognitive impairment, and dementia.

The method can further include obtaining a memory impairment score from the subject by administering a memory impairment screening test to the subject. A suitable memory test is Hopkins Verbal Learning Test-Revised (HVLT-R).

In some embodiments, the method includes converting the Z-scored expression value of each biomarker into a numeric score of 1, 0.5 or 0, depending if the biomarker's expression is in the high-risk range, intermediate risk range, or low risk range, based on the reference expression values for the particular biomarker. In some instances, this score is multiplied by the biomarker's CFE (Convergent Functional Evidence) score, which serves as a weight, as not all biomarkers are equally important. See such CFE scores in Table 2. In some instances, the resulting value is then divided by the maximum possible CFE score for that particular biomarker, yielding a weighted score. In some instances, the weighted scores are added for all the biomarkers in the panel, and divided by the number of markers in the panel. In some instances, the panel score is multiplied by 100 to generate a value between 0 and 100, which can be compared to a reference score.

In some embodiments, for each biomarker in the panel, a list of existing psychiatric medications that modulate the expression of the biomarker in the direction of high memory can be identified bioinformatically. In some instances, each such medication can be given a score commensurate with the biomarker score, i.e. 1 or 0.5 or 0. In some instances, such a medication can modulate more than one biomarker. In some instances, an average score for each medication can be calculated based on its effects on the biomarkers in the panel, and multiplied that by 100, resulting in a score of 0 to 100 for each medication. In some embodiments, psychiatric medications can be matched to the expression of biomarkers in a particular patient and ranked in order of impact on the panel.

In some embodiments, large drug gene expression databases such as Connectivity Map and NIH LINCS can be interrogated, as related to particular biomarkers that are positive as high risk in the panel in a particular patient. In some instances, this can lead to an individualized drug repurposing, identifying and ranking for fit using a score. As such, a new method of use for non-psychiatric medications and nutraceuticals can be identified and used in a particular patient to reduce risk and mitigate memory dysfunction, Alzheimer's Disease and cognitive decline.

EXAMPLES

Materials and Methods

Figure 1B:
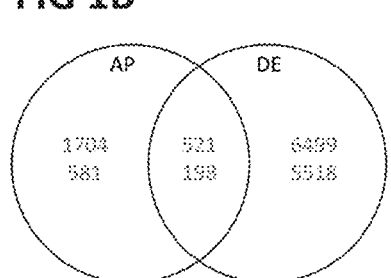
Figure 1C:
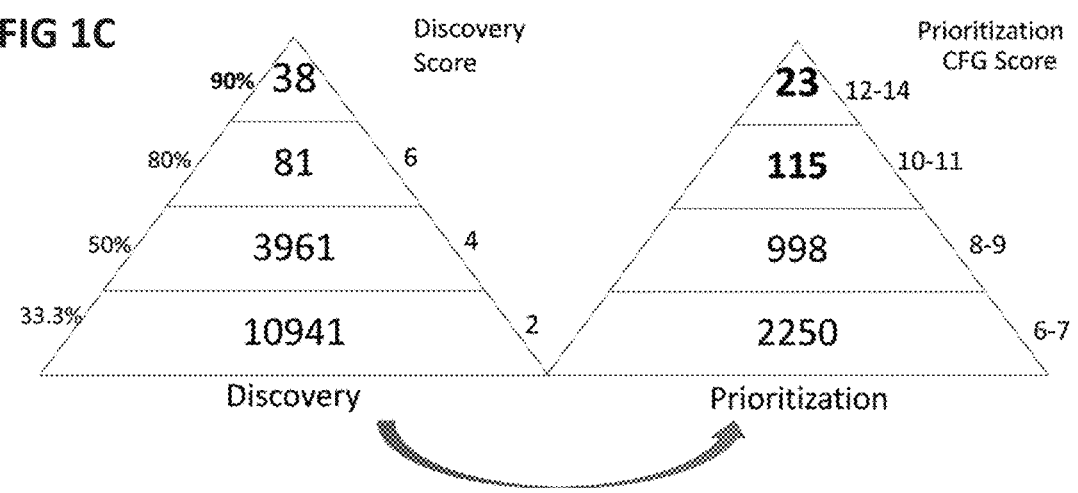

Two independent cohorts of psychiatric disorders patients, one for Discovery of candidate biomarkers, and one for Testing of top biomarkers (for predicting memory state, and predicting future positive neuropsychological testing for cognitive impairment) were used (FIG. 1, Table 1).

TABLE 1

| | | | | | | |
|---|---|---|---|---|---|---|
| | | | Aggregate demographics. Cohorts used in study. | | | |
| Cohorts | Number of subjects (number of visits) | Gender | Diagnosis | Ethnicity | Age in years at time of lab visit Mean (SD) (Range) | T-test for age at time of lab visit |
| | | | Discovery | | | |
| Discovery Cohort (Within-Subject Changes in Memory Retention) | 159 (with 496 visits) | Male = 131 (414) Female = 28 (82) | BP = 52 (187) MDD = 23 (64) SZA = 35 (97) SZ = 27 (82) PTSD = 14 (43) MOOD = 5 (14) PSYCH = 3 (9) | EA = 107 (347) AA = 47 (135) Asian = 1 (2) Hispanic = 3 (9) Biracial = 1 (3) | 50.26 (8.97) (22-66) | |
| | | | Testing | | | |
| Independent Testing Cohort For Predicting State (Low Memory Retention ≤40 at Time of Assessment) | 127 (238 visits) | Male = 97 (176) Female = 30 (62) | BP = 37 (73) MDD = 24 (48) SZA = 27 (48) SZ = 23 (42) PTSD = 12 (20) MOOD = 2 (5) PSYCH = 2 (2 | EA = 86 (162) AA = 40 (73) Asian = 1 (3) | 50.48 (8.2) (23-74) Low Memory Retention = 50.9 (10.9) Others = 50.32 (6.83) | Low Memory Retention (n = 68) vs. Others (n = 170) 0.703983 |
| Independent Testing Cohort For Predicting Trait (Future Positive Neuropsych Testing for Dementia in All Years Following Assessment) | 56 (111 visits) | Male = 47 (91) Female = 9 (20) | BP = 11 (23) MDD = 13 (26) SZA = 11 (20) SZ = 15 (30) PTSD = 5 (10) MOOD = 1 (2) | EA = 33 (64) AA = 23 (47) | 55.6 (5.0) (40-74) Neuropsych Testing Positive = 54.2 (6.05) Others = 55.8 (4.89) | Future Positive Neuropsych Testing (n = 11) vs. Others (n = 100) 0.411644 |

BP - Bipolar; MDD - Major depressive disorder; SZA - schizoaffective disorder; SZ - schizophrenia, PTSD - post-traumatic stress disorder.

Figure 6:
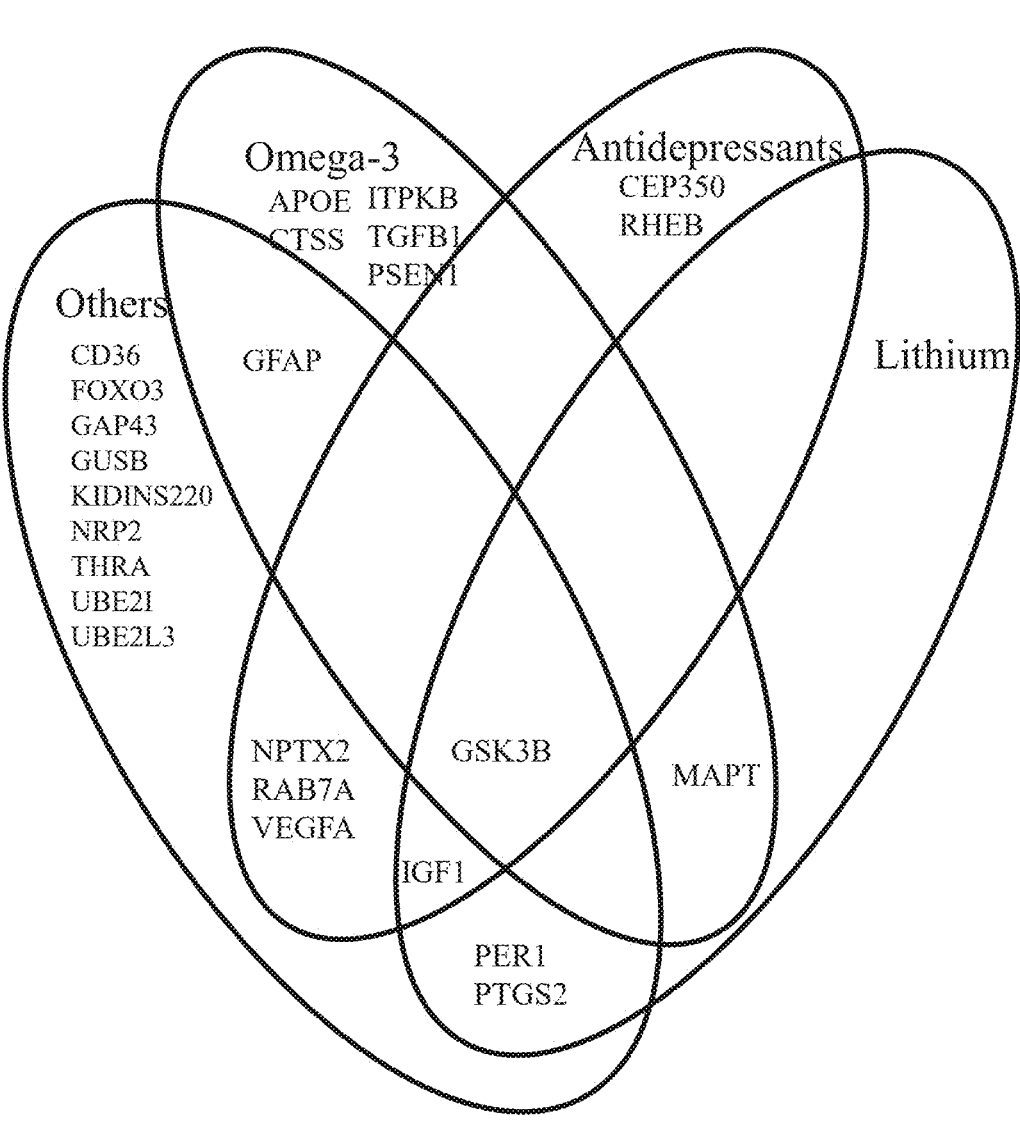
FIG. 6 is a schematic diagram depicting the matching of patients to drugs, the pharmacogenomics.

The psychiatric subjects were part of a larger longitudinal cohort of adults. Subjects were recruited from the patient population at the Indianapolis VA Medical Center. All subjects understood and signed informed consent forms detailing the research goals, procedure, caveats and safeguards, per IRB approved protocol. Subjects completed diagnostic assessments by an extensive structured clinical interview—Diagnostic Interview for Genetic Studies, and up to six testing visits, 3-6 months apart or whenever a new psychiatric hospitalization occurred. At each testing visit, they received a series of rating scales, including a Hopkins Verbal Learning Test (HVLT-R, see FIG. 6), and blood was drawn. Whole blood (10 ml) was collected in two RNA-stabilizing PAXgene tubes, labeled with an anonymized ID number, and stored at –80° C. in a locked freezer until the time of future processing. Whole-blood RNA was extracted for microarray gene expression studies from the PAXgene tubes, as detailed below.

For this study, the within-subject longitudinal discovery cohort, from which the biomarker data were derived, consisted of 159 subjects (131 males, 28 females) with multiple testing visits (a total of 496), who each had at least one 20% change in the Retention measure of HVLT from one consecutive testing visit to another.

The independent test cohort for predicting state (Low Memory Retention) consisted of 127 subjects (97 males, 30 females), demographically matched with the discovery cohort, with one or more testing visits (for a total of 238 visits). Low Memory Retention was defined as a score of ≤40 (FIG. 1, Table 1).

The independent test cohort for predicting trait (future positive neuropsychological testing for cognitive impairment) consisted of 56 subjects (47 males, 9 females), demographically matched with the discovery cohort, with one or more testing visits in our lab (for a total of 111 visits). Positive neuropsychological testing was defined as a diagnosis of MCI, ADRD (Alzheimer Disorder Related Dementia), or other dementia upon neuropsychological testing done in a clinical setting, triggered by clinical concerns as part of regular clinical care (FIG. 1, Table 1).

Medications. The subjects in the discovery cohort were all diagnosed with various psychiatric disorders (see, Table 1), and had various medical co-morbidities. Their medications were listed in their electronic medical records, and documented at the time of each testing visit. Medications can have a strong influence on gene expression. However, the discovery of differentially expressed genes was based on within-subject analyses, which factor out not only genetic background effects but also minimizes medication effects, as the subjects rarely had major medication changes between visits. Moreover, there was no consistent pattern of any particular type of medication, as the subjects were on a wide variety of different medications, including both psychiatric and non-psychiatric. Furthermore, the independent validation and testing cohorts' gene expression data was Z-scored by gender and diagnosis before being combined, to normalize for any such effects.

RNA extraction. Whole blood (2.5-5 ml) was collected into each PaxGene tube by routine venipuncture. PaxGene tubes contain proprietary reagents for the stabilization of RNA. RNA was extracted and processed as previously described (Niculescu et al., *Mol. Psychiatry* 2015 20(11): 1266-1285; Levey et al., *Mol. Psychiatry* 2016 21(6): 768-785; Le-Niculescu et al., *Mol. Psychiatry* 2013 18(12): 1249-1264).

Microarray. Microarray work was carried out as previously described (Niculescu et al., *Mol. Psychiatry* 2015 20(11): 1266-1285; Levey et al., 2016; Le-Niculescu et al., 2013.

For biomarker discovery, the subject's score from the HVLT-DR Retention measure was assessed at the time of blood collection (FIG. 1). Using a 20% change threshold in Retention, differences in gene expression between visits were analyzed, using a powerful within-subject design, then an across-subjects summation (FIG. 1).

Data was analyzed in two ways: an Absent-Present (AP) approach, and a differential expression (DE) approach. The AP approach may capture turning on and off of genes, and the DE approach may capture gradual changes in expression. A powerful within-subject design, then an across-subjects summation score was used for probe sets. Affymetrix microarray data was imported as CEL. files into Partek Genomic Suites 6.6 software package (Partek Incorporated, St Louis, MI, USA). Using only the perfect match values, a robust multi-array analysis (RMA) by gender and diagnosis, background corrected with quantile normalization and a median polish probe set summarization of all chips, was performed to obtain the normalized expression levels of all probe sets for each chip. Then, to establish a list of differentially expressed probe sets a within-subject analysis was conducted using a fold change in expression of at least 1.2 between high stress and low stress visits within each subject. Probe sets that had a 1.2-fold change were then assigned either a 1 (increased in high stress) or a −1 (decreased in high stress) in each comparison. These values were then summed for each probe set across all the comparisons and subjects, yielding a range of raw scores. The probe sets above the 33.3% of scores received an internal score of 2 points, those above 50% received 4 points, and those above 80% received 6 points. R scripts were developed to automate and conduct all these large dataset analyses in bulk, and checked against human manual scoring.

Gene Symbol for the probe sets were identified using NetAffyx (Affymetrix) for Affymetrix HG-U133 Plus 2.0 GeneChips, followed by GeneCards to confirm the primary gene symbol. In addition, for those probe sets that were not assigned a gene symbol by NetAffyx, GeneAnnot or UCSC were used to obtain gene symbols, followed by GeneCard. Genes were then scored using the manually curated CFG databases as described below (FIG. 1).

For prioritization using Convergent Functional Genomics (CFG) was used for prioritization. Databases of the human gene expression/protein expression studies (postmortem brain, peripheral tissue/fluids: CSF, blood and cell cultures), human genetic studies (association, copy number variations and linkage), and animal model gene expression and genetic studies, published to date on psychiatric disorders was manually curated. Only findings deemed significant in the primary publication, by the study authors, using their particular experimental design and thresholds, were included in the databases. The databases include only primary literature data and do not include review papers or other secondary data integration analyses to avoid redundancy and circularity. These large and constantly updated databases have been used in a CFG cross validation and prioritization platform (FIG. 1). For this study, data from 213 papers on AD were present in the databases at the time of the CFG analyses (August 2018) (human genetic studies—62, human brain tissue studies—49, human peripheral tissue/fluids—83, non-human genetic studies—4, non-human brain tissue studies—13, non-human peripheral tissue/fluids—2). Analyses were performed as previously described (Niculescu et al., *Mol. Psychiatry* 2015; 20(11): 1266-1285; Levey et al., *Mol. Psychiatry* 2016 21(6): 768-785).

Biomarkers to be carried forward were selected after the prioritization step, using as threshold a CFG score≥10 (n=138 probe sets, 112 genes). Of these, the top candidate biomarkers had a CFG score≥12 (n=23 probe sets, 18 genes). In Step 3, testing, Low Memory Retention state, and future positive neuropsychological testing for cognitive impairment were then predicted in independent cohorts.

In Step 3, testing, the test cohort for predicting Low Memory Retention (state), and the test cohort for predicting Future Positive Neuropsychological Testing (trait), were assembled out of data that was RMA normalized by gender and diagnosis. The cohort was completely independent from the discovery and validation cohorts, there was no subject overlap with them. Phenomic (clinical) and gene expression markers used for predictions were Z scored by gender and diagnosis, to be able to combine different markers into panels and to avoid potential artefacts due to different ranges of expression in different gender and diagnoses. Markers were combined by simple summation of the increased risk markers minus the decreased risk markers. Predictions were performed using R-studio. For cross-sectional analyses, marker expression levels, z-scored by gender and diagnosis were used. For longitudinal analyses, four measures were combined: marker expression levels, slope (defined as ratio of levels at current testing visit vs. previous visit, divided by time between visits), maximum levels (at any of the current or past visits), and maximum slope (between any adjacent current or past visits). For decreased markers, the minimum rather than the maximum were used for level calculations. All four measures were Z-scored, then combined in an additive fashion into a single measure. The longitudinal analysis was carried out in a sub-cohort of the testing cohort consisting of subjects that had at least two test visits.

Predicting State Low Memory. Receiver-operating characteristic (ROC) analyses between marker levels and memory state were performed by assigning subjects visits with a HVLT Retention score of ≤40 into the Low Memory category (using the pROC package of R; Xavier Robin et al. BMC Bioinformatics 2011) (see, FIG. 3). Additionally, a one-tailed t-test was performed between Low Memory group vs. the rest, and Pearson R (one-tail) was calculated between Memory scores and markerlevels.

Predicting Trait Future Positive Neuropsychological Testing for Cognitive Impairment. Analyses was conducted for predicting future positive neuropsychological testing performed as part of routine clinical care in subjects that had follow-up in the VA system using electronic medical records follow-up data of the study subjects (up to 12.81 years from initial visit). Analyses between genomic and phenomic markers measures (cross-sectional, longitudinal) at a specific testing visit and future positive neuropsychological test were performed as described below, based on assigning if subjects had a future positive neuropsychological test for cognitive impairment or not. A Cox regression was performed using the time in days from the lab testing visit date to the positive neuropsychological testing date. The hazard ratio was calculated such that a value greater than 1 always indicated increased risk for positive neuropsychological testing, regardless if the biomarker was increased or decreased in expression. A hazard ratio (also called odds ratio, O.R.) can be calculated using biomarker expression information as a means for predicting risk of future development of Alzheimer's and related disorders. Additionally, a Pearson R (one-tail) correlation was performed between positive neuropsychological testing frequency (number of positive neuropsychological tests divided by duration of follow-up) and marker levels.

Pharmacogenomics. Which of the top biomarkers from Table 3 (n=38 probe sets) known to be modulated by existing drugs were analyzed using the CFG databases, and using Ingenuity Drugs analyses (Tables 2 and 3).

TABLE 2

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involvement in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| RAB7A RAB7A, member RAS oncogene family | 227602_at | (I) AP/2 43.8% (I) DE/4 69.6% | 7 | ALL L: (17/111) 0.66/1.73E−02 Gender Dx F-BP L: (2/9) 1/2.02E−02 M-BP L: (1/27) 1/4.76E−02 M-PSYCHOSIS L: (8/27) 0.76/1.68E−02 M-SZ L: (5/14) 0.8/3.59E−02 M-SZA C: (12/33) 0.67/4.98E−02 | Gender Male C: (7/91) 2.51/3.08E−02 | BP Brain arousal depression MDD neuropathic pain | TCA Valproate | 21 |
| NPC2 Niemann-Pick disease, type C2 | 200701_at | (D) DE/6 80.8% | 8 | ALL L: (17/111) 0.65/2.38E−02 Gender Male L: (12/79) 0.65/4.65E−02 Gender Dx M-MDD L: (3/18) 0.96/7.58E−03 M-SZA L: (3/13) 0.9/2.13E−02 | | Aging alcohol SZ | | 20 |
| TGFB1 transforming growth factor beta 1 | 203084_at | (I) AP/4 54.5% | 9 | ALL C: (68/238) 0.58/2.88E−02 Gender Male C: (53/176) 0.6/2.29E−02 Gender Dx M-PTSD C: (4/10) 1/5.26E−03 M-SZ C: (15/34) 0.68/3.99E−02 | | Aging ASD BP Chronic stress Depression Longevity Pain Phencyclidine PTSD Suicide SZ | Omega-3 fatty acids | 19 |
| GAP43 growth associated protein 43 | 204471_at | (I) DE/4 50.8% | 7 | Gender Dx M-SZA L: (3/13) 0.867/3.15E−02 | ALL C: (11/111) 2.07/2.08E−02 L: (3/50) 6.14/1.51−02 Gender Male C: (7/91) 2.94/1.17E−02 L: (3/43) 5.54/1.47−02 Gender-Dx M-Psychosis L: (2/22) 5.4/2.96−02 M-SZ L: (2/13) 4.08/3.83−02 | BP depression SZ stress | Valproate Benzodiazepines | 19 |

TABLE 2-continued

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involve- ment in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| ARSB arylsulfatase B | 1554030_at | (I) DE/6 91.7% | 6 | ALL L: (17/111) 0.72/2.19E−03 Gender Male L: (12/79) 0.74/4.92E−03 Gender Dx F-BP L: (2/9) 0.93/3.95E−02 M-PSYCHOSIS L: (8/27) 0.88/1.04E−03 M-SZ L: (5/14) 0.8/3.59E−02 M-SZA L: (3/13) 1/5.61E−03 | | Alcohol Depression MDD Suicide | | 18 |
| PER1 period circadian clock 1 | 242832_at | (I) DE/4 61.3% | 6 | Gender Female C: (15/62) 0.7/9.17E−03 Gender Dx F-BP C: (6/19) 0.83/1.13E−02 M-BP L: (1/27) 1/4.76E−02 | Gender Male L: (3/43) 5.2/4.97E−03 | Alcohol Anxiety ASD Autism BP Circadian abnormalities Depression MDD PTSD Sleep Duration Suicide SZ | Lithium Clozapine Quetiapine Avibactam | 18 |
| GUSB glucuronidase, beta | 202605_at | (D) DE/4 55.7% | 8 | ALL L: (17/111) 0.65/2.16E−02 Gender Female L: (5/32) 0.79/2.29E−02 Gender Dx F-BP C: (6/19) 0.81/1.76E−02 M-MDD L: (3/18) 0.89/1.91E−02 | | Aging Methamphetamine | Clozapine | 18 |
| MAPT microtubule associated protein tau | 203930_s_at | (I) DE/2 33.7% | 10 | | ALL L: (11/111) 1.96/2.95E−02 Gender Male C: (7/91) 3.54/4.62E−02 Gender Dx M-PSYCHOSIS C: (5/47) 2.84/3.34E−02 M-SZ C: (4/27) 4.65/4.06E−02 | Aging Alcohol Intellect MDD Methamphetamine Phencyclidine Stress Suicide SZ | Lithium Omega-3 fatty acids | 18 |
| FCGR1A Fc fragment of IgG, high | 216951_at | (I) DE/4 64.6% | 7 | | ALL L: (3/49) 20/3.50−02 | | | 17 |

TABLE 2-continued

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involve- ment in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| affinity Ia, receptor (CD64) | | | | | Gender Male L: (3/40) 15.4/4.37E−02 | | | |
| UBE2L3 ubiquitin conjugating enzyme E2L3 | 200682_s_at | (D) DE/6 91% | 4 | ALL L: (17/111) 0.63/4.13E−02 Gender Male L: (12/79) 0.65/4.92E−02 Gender Dx M-BP C: (10/54) 0.7/2.25E−02 M-SZA L: (3/13) 0.9/2.13E−02 | | Aging Alcohol ASD Depression Stress SZ | Clozapine | 16 |
| NKTR natural killer cell triggering receptor | 1570342_at | (D) AP/6 85% | 4 | ALL C: (68/238) 0.59/1.40E−02 Gender Male C: (53/176) 0.62/5.55E−03 Gender Dx M-BP C: (10/54) 0.68/3.56E−02 M-PSYCHOSIS C: (27/67) 0.63/3.19E−02 M-PSYCHOSIS L: (8/27) 0.72/3.55E−02 M-SZ C: (15/34) 0.72/1.38E−02 M-SZ L: (5/14) 1/1.35E−03 | | Alcohol BP Depression MDD Social Isolation Stress Suicide SZ | | 16 |
| RHEB Ras homolog enriched in brain | 243008_at | (D) AP/6 84.4% (D) DE/4 64.1% | 4 | | ALL C: (11/111) 1.51/3.05E−02 Gender Male C: (7/91) 1.63/2.46E−02 Gender Dx M-PSYCHOSIS C: (5/47) 2.12/5.45E−03 L: (2/22) 9.69/1.68E−02 M-SZ C: (4/27) 1.82/1.78E−02 L: (2/13) 6.22/3.32E−02 | Suicide Pain SZ | Antidepressants | 16 |
| PTGS2 prostaglandin- endoperoxide synthase 2 (prostaglandin G/H | 1554997_a_at | (D) DE/4 76% | 10 | Gender Dx M-PTSD C: (4/10) 0.88/2.75E−02 | | Aggression Alcohol ASD BP Chronic Fatigue | Antipsychotics Lithium Vorinostat | 16 |

TABLE 2-continued

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involve- ment in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| synthase and cyclooxygenase) | | | | | | Syndrome Depression Depression- Related MDD Neurological Pain Phencyclidine Social Isolation Stress Stress Substances/ Addictions Suicide | | |
| RGS10 regulator of G-protein signaling 10 | 214000_s_at | (I) DE/4 63.5% | 6 | ALL L: (17/111) 0.7/3.89E−03 Gender Male L: (12/79) 0.74/4.73E−03 Gender Dx F-BP L: (2/9) 0.93/3.95E−02 M-BP L: (1/27) 1/4.76E−02 M-MDD L: (3/18) 0.87/2.53E−02 M-SZ C: (15/34) 0.68/3.70E−02 | | Aging BP Female specific interpersonal- traumas Methamphetamine Post- Deployment PTSD PTSD Stress Suicide SZ | | 16 |
| MAPT microtubule associated protein tau | 203928_x_at | (I) DE/4 57.5% | 10 | Gender Dx F-BP C: (6/19) 0.81/1.76E−02 | | Aging Alcohol Intellect MDD Methamphetamine Phencyclidine Stress Suicide SZ | Lithium Omega-3 fatty acids | 16 |
| ITPKB inositol- trisphosphate 3-kinase B | 232526_at | (I) DE/4 51.9% | 6 | ALL L: (17/111) 0.73/1.60E−03 Gender Male L: (12/79) 0.7/1.44E−02 Female L: (5/32) 0.79/2.29E−02 Gender Dx M-BP L: (1/27) 1/4.76E−02 | | Aging Alcohol MDD Phencyclidine Stress Suicide, SZ SZ | | 16 |
| KIDINS220 kinase D- interacting substrate 220 kDa | 214932_at | (I) DE/4 51.9% | 6 | Gender Dx F-BP L: (2/9) 0.93/3.95E−02 | Gender Male C: (7/91) 2.49/3.78E−02 Gender-Dx M-BP | Alcohol MDD Psychosis Pain Suicide Stress | Clozapine | 16 |

TABLE 2-continued

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involve-ment in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| GSK3B glycogen synthase kinase 3 beta | 209945_s_at | (D) DE/4 50.3% | 10 | Gender Dx M-SZA L: (3/13) 0.93/1.40E−02 | C: (2/16) 6.06/4.18−02 | Aging Alcohol ASD BP BP, SZ MDD Stress Suicide SZ | Astaxanthin-DHA Antipsychotics Lithium Omega-3 fatty acids Ketamine lipoteichoic acid Valproate enzastaurin, glycogen synthase kinase-3beta inhibitor | 16 |
| SERTAD3 SERTA domain containing 3 | 219382_at | (D) DE/6 81.4% | 5 | Gender Female L: (5/32) 0.79/2.29E−02 Gender Dx F-BP C: (6/19) 0.81/1.76E−02 F-PSYCHOSIS L: (2/13) 1/1.50E−02 F-SZA L: (2/8) 1/2.28E−02 | | Alcohol ASD Aging | | 15 |
| APOE apolipoprotein E | 212884_x_at | (D) AP/2 34.1% | 11 | Gender Dx M-PTSD C: (4/10) 0.88/2.75E−02 Gender Dx M-SZ L: (5/14) 0.89/9.82E−03 | | Aggression Aging Alcohol Anxiet ASD BP Brain arousal MDD PTSD Stress Suicide SZ TBI | Omega-3 fatty acids | 15 |
| UBE2I ubiquitin conjugating enzyme E21 | 233360_at | (D) DE/6 86.8% | 6 | Gender Dx F-PSYCHOSIS L: (2/13) 0.91/3.78E−02 F-SZA L: (2/8) 0.92/4.78E−02 | | Aging Alcohol ASD Hallucinations Mood State Stress | Clozapine | 14 |
| FOXO3 forkhead box O3 | 231548_at | (I) AP/2 38.9% (I) DE/6 82.3% | 4 | Gender Dx F-SZA C: (5/15) 0.78/4.32E−02 | Gender Dx M-PSYCHOSIS C: (5/47) 4.14/4.58E−02 | BP Cocaine Longevity PTSD Stress Suicide | Clozapine | 14 |
| THRA thyroid hormone receptor, alpha | 214883_at | (I) DE/4 61.3% | 8 | Gender Dx F-BP C: (6/19) 0.79/2.18E−02 M-BP | | Alcohol PTSD Stress Suicide SZ | 3,5-diiodothyropropionic acid,denosumab/ levothyroxine, amiodarone, | 14 |

TABLE 2-continued

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involvement in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| ITPKB inositol-trisphosphate 3-kinase B | 1554306_at | (D) AP/4 61.1% (D) DE/4 55.7% | 6 | L: (1/27) 1/4.76E−02 Gender Female L: (5/32) 0.81/1.37E−02 Gender Dx F-BP C: (6/19) 0.91/2.50E−03 F-BP L: (2/9) 1/2.02E−02 | | Acute Stress Aging Alcohol ASD BP MDD Neurological Suicide SZ | levothyroxine, dextrothyroxine, L-triiodothyronine Omega-3 fatty acids | 14 |
| IGF1 insulin-like growth factor 1 (somatomedin C) | 209542_x_at | (I) DE/4 54.1% | 8 | Gender Dx F-BP C: (6/19) 0.79/2.18E−02 | | Aggression Aging Alcoho Anxiety BP Depression Longevity PTSD SZ | Lithium Clozapine Fluoxetine (SSRI), Venlafaxine (SNRI) MEDI-573, BI836845 | 14 |
| NPTX2 neuronal pentraxin II | 213479_at | (I) DE/4 52.5% | 8 | Gender Dx F-BP L: (2/9) 0.93/3.95E−02 | | Alcohol Brain arousal Cocaine Depression MDD MDD, SZ Mood Disorders NOS Stress Suicide | Clozapine Fluoxetine | 14 |
| GSTM3 glutathione S-transferase mu 3 (brain) | 235867_at | (D) DE/4 52.1% | 8 | Gender Dx F-SZA C: (5/15) 0.78/4.32E−02 | | BP MDD SZ | | 14 |
| BACE1 Beta-Secretase 1 | 222463_s_at | (I) DE/2 44.8% | 8 | | Gender Male C: (7/91) 1.97/3.78E−02 | MDD Stress Suicide | | 14 |
| PSEN1 presenilin 1 | 203460_s_at | (D) DE/4 54.5% | 9 | | | Aging Alcohol Autism Depression Emotional Stability Neuroticism Suicide SZ | Omega-3 fatty acids | 13 |
| GFAP glial fibrillary acidic protein | 203540_at | (I) DE/2 34.3% | 9 | Gender Dx F-BP C: (6/19) 0.77/3.28E−02 | | Addictions Alcohol BP MDD Stress Suicide SZ Yohimbine | Omega-3 fatty acids Clozapine | 13 |

TABLE 2-continued

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involve-ment in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| TREM2 triggering receptor expressed on myeloid cells 2 | 219725_at | (I) DE/2 37.6% | 11 | | | BP SZ | | 13 |
| NOCT nocturnin | 220671_at | (D) AP/4 69.5% | 6 | Gender Dx F-PTSD C: (3/9) 1/1.01E−02 | | PTSD Post-Deployment PTSD | | 12 |
| CEP350 centrosomal protein 350 kDa | 204373_s_at | (D) DE/4 67.1% | 6 | | Gender Dx M-PSYCHOSIS L: (2/22) 54.6/3.77E−02 | Autism BP Cocaine Depression PTSD Stress Suicide SZ | Antidepressants, Fluoxetine | 12 |
| PPP2R2B protein phosphatase 2, regulatory subunit B, beta | 205643_s_at | (I) DE/4 63.5% | 6 | Gender Dx F-BP L: (2/9) 1/2.02E−02 | | ADHD Aging Alcohol ASD Circadian abnormalities Longevity PTSD Suicide SZ | | 12 |
| NRP2 neuropilin 2 | 222877_at | (I) DE/4 61.3% | 6 | Gender Dx M-MDD L: (3/18) 0.98/5.43E−03 | | Longevity MDD Phencyclidine Stress | Clozapine | 12 |
| CTSS cathepsin S | 232617_at | (D) DE/4 56.9% | 8 | | | Aging Alcohol ASD BP Brain arousal Pain Suicide | Omega-3 fatty acids | 12 |
| VEGFA vascular endothelial growth factor A | 211527_x_at | (I) DE/2 45.3% | 8 | Gender Dx M-MDD C: (11/38) 0.7/2.57E−02 | | Alcohol Anxiety BP Chronic Stress Depression Hallucinations Intellect MDD Pain MSK Stress Suicide SZ | Antipsychotics Fluoxetine Steroids | 12 |
| MAPT microtubule associated protein tau | 233117_at | (I) DE/2 44.2% | 10 | | | Aging Alcohol Intellect MDD Methamphetamine Phencyclidine Stress Suicide SZ | Lithium Omega-3 fatty acids | 12 |

TABLE 2-continued

Top Biomarkers. Convergent Functional Evidence for Relevance to Short-Term Memory Tracking and Alzheimer Disease (AD).

| Genesymbol/ Gene name | Probeset | Step 1 Discovery in blood (Direction of change tracking increased memory) method/ score/ % up to 6 pts | Step 2 External CFG evidence for involvement in AD score up to 12 pt | Step 3 Best significant prediction of state Low memory retention ROC AUC/ p-value up to 6 pts ALL 4 pts gender 2 pts gender/Dx | Step 3 Best significant predictions of trait future positive neuropsych OR/OR p-value Up to 6 pts ALL 4 pts gender 2 pts gender/Dx | Other psychiatric and related disorders evidence (change in opposite direction to increased memory) | Pharmacogenomics Drugs that modulate the biomarker (Change in Same Direction to Increased Memory) | CFE polyevidence score |
|---|---|---|---|---|---|---|---|---|
| GSK3B glycogen synthase kinase 3 beta | 240562_at | (I) DE/2 39.2% | 10 | | | Aging Alcohol ASD BP MDD Methamphetamine Psychological Stress Stress Suicide SZ Yohimbine | Antipsychotics Antipsychotics Pregnenolone sulfate Fluoxetine (SSRI) Lithium mood stabilizing drugs Valproate | 12 |
| GSK3B glycogen synthase kinase 3 beta | 242336_at | (D) AP/2 34.1% | 10 | | | Aging Alcohol ASD BP BP,SZ MDD Stress Suicide SZ | Astaxanthin-DHA Antipsychotics Lithium Omega-3 fatty acids Ketamine lipoteichoic acid Valproate enzastaurin, glycogen synthase kinase-3beta inhibitor | 12 |
| BACE1 Beta-Secretase 1 | 224335_s_at | (I) DE/2 43.1% | 8 | | | MDD Stress Suicide | | 10 |

Bold - top biomarkers after discovery and prioritization (n = 23, CFG ≥ 12)). Underlined - best predictor in a category after testing of the longer list candidate biomarkers after discovery and prioritization (n = 138, CFG ≥ 10), as depicted in Figure 3. We tabulated into a convergent functional evidence (CFE) score all the evidence from discovery (up to 6 points), prioritization (up to 12 points), testing (State Memory Retention State and Trait Future Positive Neuropsychological Testing (up to 6 points each if significantly predicts in all subjects, 4 points if predicts by gender, 2 points if predicts in gender/diagnosis subgroups). The goal is to highlight, based on the totality of our data and of the evidence in the field to date, biomarkers that have all around evidence: track memory; are implicated in AD, and predict memory state and future dementia. Such biomarkers merit priority evaluation in future clinical trials. As depicted in Figure 1B, the top row of values-increased in expression (I) in high memory, bottom row of values-decreased in expression (D) in high memory. DE - differential expression, AP - Absent/Present. "C" - Cross-sectional analyses; "L" - Longitudinal analyses, using levels and slopes from multiple visits. In All, by Gender, and personalized by Gender and Diagnosis (Gender/Dx). "DE" - differential expression, "AP" - Absent/Present. For Step 3 Predictions, C-cross-sectional (using levels from one visit), L - longitudinal. "M" - males, "F" - Females. "MDD" - depression, "BP" - bipolar, "SZ" - schizophrenia, "SZA" - schizoaffective, PSYCHOSIS - schizophrenia and schizoaffective combined, "PTSD" - post-traumatic stress disorder.

TABLE 3

Matching with drugs. Evidence for modulation by drugs in same direction as increased memory retention (see also, FIG. 5).

| Genesymbol/ Gene name | Probesets | Step 1 Discovery in Blood (Direction of Change tracking Memory Increase) Method/ Score/% Up to 6 pts | Step 2 External CFG Evidence For Involvement in AD Score Up to 12 pts | Lithium | Omega-3 | Anti-depressants | Other drugs |
|---|---|---|---|---|---|---|---|
| APOE apolipoprotein E | 212884_x_at | (D) AP/2 34.1% | 11 | | (D) Lymphocytes (males) Omega-3 fatty acids[318] | | |
| GSK3B glycogen synthase kinase | 242336_at 209945_s_at | (D) AP/2 34.1% (D) | 10 | (D) olfactory neurons Lithium[298] | (D) PFC (females) Omega-3 | | (D) HIP Ketamine[320] (D) |

TABLE 3-continued

Matching with drugs. Evidence for modulation by drugs in same direction as increased memory retention (see also, FIG. 5).

| Genesymbol/ Gene name | Probesets | Step 1 Discovery in Blood (Direction of Change tracking Memory Increase) Method/ Score/% Up to 6 pts | Step 2 External CFG Evidence For Involvement in AD Score Up to 12 pts | Lithium | Omega-3 | Anti-depressants | Other drugs |
|---|---|---|---|---|---|---|---|
| 3 beta | | DE/4 50.3% | | Lithium[319] | fatty acids[318] (D) HIP Alzheimer's Disease Astaxanthin-DHA[43] | | HIP lipoteichoic acid[301] (D) Caudate putamen Valproate[222] (D) Frontal Cortex Antipsychotics[321] Enzastaurin |
| MAPT microtubule associated protein tau | 203930_s_at 233117_at 203928_at | (I) DE/2 33.7% (I) DE/2 44.2% (I) DE/4 57.5% | 10 | (I) Schneider 2 (S2) cells Lithium[322] | (I) HIP (males) Omega-3 fatty acids[318] | | |
| PTGS2 prostaglan dinendoperoxide synthase 2 (prostaglandin G/H synthase and cyclooxygenase) | 1554997_a_at | (D) DE/4 76% | 10 | (D) PBMC Lithium[165] | | | (D) Serum, HIP Vorinostat[323] (D) PBMC Antipsychotics[165] Acetaminophen NSAIds |
| GFAP glial fibrillary acidic protein | 203540_at | (I) DE/2 34.3% | 9 | | (I) Brain Omega-3 fatty acids[324] | | (I) AMY, HIP, PFC Clozapine[171] |
| PSEN1 presenilin 1 | 203460_s_at | (D) DE/4 54.5% | 9 | | (D) Lymphocytes (females) Omega-3 fatty acids[318] | | tarenflurbil |
| TGFB1 transforming growth factor beta 1 | 203084_at | (D) AP/4 54.5% | 9 | | (D) Lymphocytes (females) Omega-3 fatty acids[318] | | dalantercept, fresolimumab, LY3200882, MSB0011359C |
| BACE1 Beta-Secretase 1 | 222463_s_at 224335_s_at | (I) DE/6 44.8% (I) DE/6 43.1% | 8 | | | | |
| CTSS cathepsin S | 232617_at | (D) DE/4 56.9% | 8 | | (D) Lymphocytes (females) Omega-3 fatty acids[318] | | |
| GUSB glucuronidase, beta | 202605_at | (D) DE/4 55.7% | 8 | | | | (D) VT Clozapine[171] |
| IGF1 insulin-like growth factor 1 (somatomedin C) | 209542_x_at | (I) DE/4 54.1% | 8 | (I) lymphoblastoid cell lines Lithium[325] | | (I) HIP Fluoxetine (SSRI), Venlafaxine (SNRI)[326] | (I) VT Clozapine[171] |
| NPTX2 neuronal pentraxin II | 213479_at | (I) DE/4 52.5% | 8 | | | (I) HIP Fluoxetine[327] | (I) VT Clozapine[171] |
| THRA thyroid hormone receptor, alpha | 214883_at | (I) DE/4 61.3% | 8 | | | | thyroxine |

TABLE 3-continued

Matching with drugs. Evidence for modulation by drugs in same direction as increased memory retention (see also, FIG. 5).

| Genesymbol/ Gene name | Probesets | Step 1 Discovery in Blood (Direction of Change tracking Memory Increase) Method/ Score/% Up to 6 pts | Step 2 External CFG Evidence For Involvement in AD Score Up to 12 pts | Lithium | Omega-3 | Anti-depressants | Other drugs |
|---|---|---|---|---|---|---|---|
| VEGFA vascular endothelial growth factor A | 211527_x_at | (I) DE/2 45.3% | 8 | | | (I) Cortex Fluoxetine[328] | (I) Plasma Antipsychotics[204] (I) Blood Steroid[329] |
| GAP43 growth associated protein 43 | 204471_at | (I) DE/4 50.8% | 7 | | | | (I) Human astrocyte-derived cells (U-87 MG) Valproate[330] (I) HIP Benzodiazepines[331] |
| RAB7A RAB7A, member RAS oncogene family | 227602_at | (I) AP/2 43.8% (I) DE/4 69.6% | 7 | | | (I) basal forebrain TCA[332] | (I) Caudate putamen Valproate[222] |
| KIDINS220 kinase D-interacting substrate 220 kDa | 214932_at | (I) DE/4 51.9% | 6 | | | | (I) VT Clozapine[171] |
| CD36 CD36 molecule (thrombospondin receptor) | 242197_x_at | (D) DE/4 56.9% | 6 | | | | (D) Lymphocytes Benzodiazepines[331] |
| CEP350 centrosomal protein 350 kDa | 204373_s_at | (D) DE/4 67.1% | 6 | | | (D) AMY Antidepressants, Fluoxetine[225] | |
| ITPKB inositol-triphosphate 3-kinase B | 1554306_at | (D) AP/4 61.1% (D) DE/4 55.7% | 6 | | (D) lymphocytes (males) Omega-3 fatty acids[318] | | |
| NRP2 neuropilin 2 | 222877_at | (I) DE/4 61.3% | 6 | | | | (I) CP Clozapine[171] |
| PER1 period circadian clock 1 | 242832_at | (I) DE/4 61.3% | 6 | (I) Cerebral cortex (right) Lithium[333] (I) lymphoblastoid cell lines (LCLs) derived Lithium[334] | | | (I) VT Clozapine[171] (I) AMY Quetiapine[335] |
| UBE21 ubiquitin conjugating enzyme E2I | 233360_at | (D) DE/6 86.8% | 6 | | | | (D) VT Clozapine[171] |
| FOXO3 forkhead box O3 | 231548_at | (I) AP/2 38.9% (I) DE/6 82.3% | 4 | | | | (I) Lymphocytes, VT Clozapin[171] |
| RHEB Ras homolog enriched in brain | 243008_at | (D) AP/6 84.4% (D) DE/4 64.1% | 4 | | | | (D) NR1[336] |

TABLE 3-continued

Matching with drugs. Evidence for modulation by drugs in same direction as increased memory retention (see also, FIG. 5).

| Genesymbol/ Gene name | Probesets | Step 1 Discovery in Blood (Direction of Change tracking Memory Increase) Method/ Score/% Up to 6 pts | Step 2 External CFG Evidence For Involvement in AD Score Up to 12 pts | Lithium | Omega-3 | Anti-depressants | Other drugs |
|---|---|---|---|---|---|---|---|
| UBE2L3 ubiquitin conjugating enzyme E2L 3 | 200682_s_at | (D) DE/6 91% | 4 | | | | (D) VT Clozapine[171] |

Tables 4A & 4B. Methods for Personalized Assessment of Memory State (Table 4A) and Prediction of Future Risk for Alzheimer and Related Disorders (Table 4B). Personalized by Gender and Psychiatric Diagnosis.

M—males; F—females; BP—bipolar; MDD—Major Depressive Disorder; PTSD—Post-Traumatic Stress Disorder; PSYCHOSIS—schizophrenia or schizoaffective disorder; SZ—schizophrenia; SZA—schizoaffective disorder; I—increased; D—decreased.

N—

TABLE 4A

Assessment for Memory State

| Diagnosis | Best Individual Biomarker | Direction of Change in Low Memory |
|---|---|---|
| M-BP | NAV2 | D |
| M-BP | UBE2L3 | I |
| M-MDD | CD40 | I |
| M-MDD | LOC101928123 | D |
| M-PSYCHOSIS | ARSB | D |
| M-PTSD | TGFB1 | I |
| M-SZ | NKTR | I |
| M-SZA | ARSB | D |
| M-SZA | CD36 | I |
| F-BP | CACNA1S | D |
| F-BP | ITPKB | I |
| F-PSYCHOSIS | SERTAD3 | I |
| F-PSYCHOSIS | LINC01398 | D |
| F-PTSD | NOCT | I |
| F-SZA | SERTAD3 | I |
| F-SZA | LINC01398 | D |

TABLE 4B

Prediction of Future Risk for Alzheimer's and Related Disorders

| Diagnosis | Best Individual Biomarker | Direction of Change in Low Memory |
|---|---|---|
| M-BP | KIDINS220 | D |
| M-PSYCHOSIS | CEP350 | I |
| M-PSYCHOSIS | CALHM1 | D |
| M-SZ | RHEB | I |
| M-SZ | MAPT | D |

Tables 5A-5C. New Therapeutics. Discovery of new method of use for drugs/repurposing. Table 5A. Connectivity Map (CMAP) analysis. Query for signature is done using exact Affymetrix probe sets and direction of change. Drugs that have same gene expression profile effects to our high memory retention biomarkers signatures. A score of 1 indicates the perfect match, i.e. the best potential therapeutic for increasing memory retention. Table 5B. NIH LINCS analysis using the L1000CDS2 (LINCS L1000 Characteristic Direction Signature Search Engine) tool. Query for signature is done using gene symbols and direction of change. Shown are compounds mimicking direction of change in high memory. A higher score indicates a better match. Table 5C. CRowd Extracted Expression of Differential Signatures (CREEDS) analysis. Query for signature is done using gene symbols and direction of change. Shown are compounds mimicking direction of change in high memory. A higher score indicates a better match.

Table 5A. Drug Repurposing Using Connectivity Map (CMAP from Broad Institute/MIT)

TABLE 5A1

Drugs Identified Using Gene Expression Panels of Top Biomarkers CFG ≥ 12 (n = 23 probe sets; 7 increased and 6 decreased were present in HG-U133A array used by CMAP). Panel of genes increased in expression: MAPT (2 probe sets), TREM2, GFAP, THRA, IGF1, NPTX2 Panel of genes decreased in expression: NPC2, GSK3B, GUSB, TGFB1, APOE, PSEN1

| rank | CMAP name | score | Description |
|---|---|---|---|
| 1 | verteporfin | 1 | A benzoporphyrin derivative, it is a medication used as a photosensitizer for photodynamic therapy to eliminate the abnormal blood vessels in the eye associated with conditions such as the wet form of macular degeneration. |

TABLE 5A1-continued

Drugs Identified Using Gene Expression Panels of Top Biomarkers CFG ≥ 12
(n = 23 probe sets; 7 increased and 6 decreased were present in HG-U133A
array used by CMAP).
Panel of genes increased in expression: MAPT (2 probe sets), TREM2, GFAP,
THRA, IGF1, NPTX2
Panel of genes decreased in
expression: NPC2, GSK3B, GUSB, TGFB1, APOE, PSEN1

| rank | CMAP name | score | Description |
|---|---|---|---|
| 2 | pioglitazone | 0.987 | A drug of the thiazolidinedione (TZD) class with hypoglycemic (antihyperglycemic, antidiabetic) action, used to treat diabetes. PPAR gamma agonist. There is evidence to suggest piolitazone is associated with a lower risk of dementia in type 2 diabetics. Phase 3 clinical trials failed to meet endpoints using pioglitazone as a therapeutic for MCI/AD. |
| 3 | salsolidine | 0.972 | A tetrahydroisoquinoline isolated from plants of the genus *Salsola*. Tetrahydroisoquinolines are steroselective competitive inhibitors of the enzyme MAO. They are also a competitive inhibitors of COMT. |
| 4 | sulfadimidine | 0.97 | A sulfonamide antibacterial. |
| 5 | SB-203580 | 0.968 | Specific inhibitor of p38MAPK. |
| 6 | ronidazole | 0.966 | An antiprotozoal agent used in veterinary medicine. |
| 7 | mesalazine | 0.961 | Anti-inflammatory salycilate derivative used to treat ulcerative colitis. |
| 8 | dioxybenzone | 0.946 | An organic compound used in sunscreen to block UVB and short-wave UVA rays. It is a derivative of benzophenone. |
| 9 | metamizole | 0.942 | A non-steroidal anti-inflammatory drug. |
| 10 | 8-azaguanine | 0.936 | A purine analog with antineoplastic activity. |
| 11 | sulfaphenazole | 0.935 | A long-acting sulfonamide antibiotic used in the treatment of leprosy. |
| 12 | dicoumarol | 0.933 | A naturally occurring anticoagulant drug that depletes stores of vitamin K. In general, vitamin K antagonists may have a negative influence on visual memory, verbal fluency, and brain volume. |
| 13 | tolazamide | 0.915 | An intermediate-acting, first-generation sulfonylurea with hypoglycemic activity. |
| 14 | pipemidic acid | 0.911 | A member of the pyridopyrimidine class of antibacterials. |
| 15 | NS-398 | 0.911 | A COX-2 inhibitor. May acutely prevent the suppression of hippocampal long-term plasticity by amyloid beta. |
| 16 | morantel | 0.901 | An anthelmintic drug used for the removal of parasitic worms in livestock. An inhibitor of acetylcholinesterase. |
| 17 | indapamide | 0.901 | A thiazide-like diuretic drug generally used in the treatment of hypertension, as well as decompensated heart failure. Indapamide has been shown to suppress the production of amyloid beta and improve clearance. |
| 18 | promazine | 0.893 | Blocks postsynaptic dopamine receptors D1 and D2 in the mesolimbic and medullary chemoreceptor trigger zone. Has significant interaction with multiple Alzheimer target proteins. |
| 19 | tinidazole | 0.893 | A nitroimidazole antitrichomonal agent effective against *Trichomonas vaginalis*, Entamoeba histolytica, and Giardia lamblia infections. |
| 20 | estradiol | 0.892 | An estrogen steroid hormone. There is evidence that suggests lifetime exposure to estrogen seems to lower risk of AD. Women who began estradiol treatment within one year of menopause had preserved metabolic activity in regions in and around the hippocampus. It is unclear whether above the age of 50 years, if estrogen/estradiol is protective against AD. |

TABLE 5A2

Drugs Identified Using Gene Expression Panels of Top
Biomarkers CFG ≥ 10 (n = 138 probe sets; 45 increased
and 38 decreased were present in HG-U133A array used by
CMAP).
Panel of genes increased in expression: BCAM, HFE, SLC1A7, FTL,
MAPT, GFAP, LDLR, SNCA, THRA, C4A, TREM2, CSF1, SNCA,
VEGFA, IL1A, SNCA, CSF1, NRP2, GAP43, CHAT, KIDINS220,
NPTX2, ANK1, IGF1, IGHG1, MAPT, FXYD1, LMNA, ANK1, IGHG1,
AXL, THRA, PPP2R2B, ANK1, RGS10, FCGR1A, LMNA, ITGB5,
APOA1, ZBTB16, OPHN1, ARG2, TSPAN5, AIMP2, RPL38.
Panel of genes decreased in expression: APOE, VEGFA, HSPA5,
ZFP36L1, TGFB1, NDUFA5, DKK1, NOCT, WDR45, IGF1,
CSF1R, ICAM1, VEGFA, ABCA7, GSK3B, GAPDH (2), SREBF1,
DUSP6, UQCRC1, TPK1, MICA, PSEN1, PSMA4, GUSB, NDUFS3,
BST2, TYROBP, CEP350, FDPS, MTF2, NPC2, SERTAD3, HSBP1,
SEC24A, SNRK, TRIM38, UBE2L3.

| rank | CMAP name | score | Description |
|---|---|---|---|
| 1 | levonorgestrel | 1 | Progesterone derivative used as contraceptive. Progesterone and its derivatives have some evidence for promoting brain cell growth, at least in adult rats, and some studies have shown that it can improve cognitive performance in the aging mouse. |
| 2 | aminohippuric acid | 0.955 | Non-toxic diagnostic tool to measure effective renal plasma flow. |
| 3 | meglumine | 0.933 | Meglumine, also known as megluminum or methylglucamine, belongs to the class of organic compounds known as hexoses. Often used as an excipient in pharmaceuticals. Methylglucamine orotate is a memory-improving drug, although the ortoate component was thought to be the active compound. |
| 4 | mesalazine | 0.932 | Non-steroidal anti-inflammatory drug used to treat inflammatory bowel diseases. |
| 5 | lymecycline | 0.92 | Tetracycline antibiotic; tetracyclines have been shown to have beneficial effects in neurodegenerative diseases. |
| 6 | torasemide | 0.918 | Diuretic. |
| 7 | dioxybenzone | 0.916 | Sunscreen compound. |
| 8 | ginkgolide A | 0.915 | A natural compound with neuroprotective and possible AD preventing effects. |
| 9 | rimexolone | 0.907 | Rimexolone is a derivative of prednisolone, a synthetic glucocorticoid with anti-inflammatory and immunosuppressive property. |
| 10 | ketanserin | 0.905 | Ketanserin is a selective serotonin receptor antagonist with weak adrenergic receptor blocking properties. Effective in lowering blood pressure in essential hypertension. Also inhibits platelet aggregation. Well tolerated in older patients. |
| 11 | dicloxacillin | 0.903 | A Penicillin-class antibacterial. |
| 12 | talampicillin | 0.898 | A beta lactam antibiotic from the penicillin family. |
| 13 | sulfadimidine | 0.897 | A sulfonamide antibacterial. |
| 14 | naringin | 0.892 | Naturally occurring flavinoid in citrus fruits, especially grapefruit. There is evidence in studies with rats that narigin acts through inhibition of oxidative cellular stress which attenuates autophagic stress especially in the hippocampus. Furthermore, there is evidence that ICV-STZ rats chronically treated with naringin dose dependently restored cognitive deficits. |
| 15 | naproxen | 0.891 | Nonsteroidal anti-inflammatory drug. Several large scale studies have demonstrated that long term treatment with naproxen confers no protection against cognitive decline. |
| 16 | flunixin | 0.888 | A nonsteroidal anti-inflammatory drug, analgesic, and antipyretic used in horses, cattle and pigs. |
| 17 | tubocurarine chloride | 0.887 | A neuromuscular blocker and active ingredient in curare; plant based alkaloid of Menispermaceae. There is evidence that anticholinergics in general are associated with future incidence of dementia. |
| 18 | cyanocobalamin | 0.885 | Vitamin B12. There is evidence that increased plasma levels of homocysteine (which can be caused by low levels of vitamin B12) is a strong and independent risk factor for the development of dementia and AD. |
| 19 | dequalinium chloride | 0.883 | A topical bacteriostat. There is evidence that dequalinium induces protofibril formation of alpha-synuclein. |
| 20 | meticrane | 0.882 | A sulphonamide-derivative with thiazide-like diuretic activity. |

TABLE 5A3

Drugs Identified Using Gene Expression Panels of Predictive
Biomarkers in All (n = 16 probe sets/genes; 5 increased and 11
decreased were present in HG-U133A array used by CMAP).
Panel of genes increased in expression: FCGR1A, GAP43, MAPT, HFE, RGS10,
Panel of genes decreased in expression: NDUFA5, SEC24A, PSMA4,
UBE2L3, NPC2, GUSB, TGFB1, TRIM38, CD40, ZNF345, IGF1.

| rank | CMAP name | score | Description |
|---|---|---|---|
| 1 | mesalazine | 1 | Non-steroidal anti-inflammatory drug used to treat inflammatory bowel diseases. |
| 2 | mepenzolate bromide | 0.985 | An oral, quaternary anticholinergic gastrointestinal agent used for adjunctive treatment of peptic ulcer disease. |
| 3 | ozagrel | 0.974 | Antiplatelet agent working as a thromboxane A2 synthesis inhibitor. Commonly used in the treatment of stroke. |
| 4 | protriptyline | 0.954 | A tricyclic antidepressant that increases the synaptic concentration of serotonin and/or norepinephrine. In vitro, protriptyline has been shown to inhibit acetylcholinesterase, $\beta$-secretase, amyloid $\beta$ aggregation, and glycation induced amyloid aggregation - all causal factors in AD progression (Bansode et al. 2014) |
| 5 | guanfacine | 0.945 | A selective $alpha_{2A}$-adrenoreceptor agonist that is used as an antihypertensive. It also preferentially binds postsynaptic $alpha_{2A}$-adrenoreceptors in the prefrontal cortex which allows its use in improving symptoms associated with ADHD. It is not a CNS stimulant. |
| 6 | saquinavir | 0.94 | An anti-retroviral protease inhibitor commonly used in the treatment of HIV. |
| 7 | tomatidine | 0.938 | A steroidal alkaloid that has been found in the skins and leaves of tomatoes. It suppresses NF-$\kappa$B signaling in LPS-stimulated macrophages, blocking induced expression of inducible nitric oxide synthase and COX-2. |
| 8 | eldeline | 0.936 | |
| 9 | zuclopenthixol | 0.931 | An antipsychotic agent working as an antagonist at D1 and D2 dopamine receptors. |
| 10 | fenoterol | 0.929 | A synthetic adrenergic $\beta_2$-agonist that is used as a bronchodilator and tocolytic. |
| 11 | vincamine | 0.929 | A monoterpenoid indole alkaloid obtained from the leaves of *Vinca minor* with a vasodilatory property. |
| 12 | imipenem | 0.926 | A carbapenem antibacterial. |
| 13 | isradipine | 0.924 | A second generation calcium channel blocker that is used to treat hypertension. |
| 14 | 3-hydroxy-DL-kynurenine | 0.919 | A metabolite of tryptophan, which filters UV light in the human lens. |
| 15 | amiodarone | 0.912 | A class III antiarrhythmic agent, amiodarone blocks the myocardial calcium, potassium and sodium channels in cardiac tissue, resulting in prolongation of the cardiac action potential and refractory period. In addition, this agent inhibits alpha- and beta-adrenergic receptors, resulting in a reduction in sympathetic stimulation of the heart, a negative chronotropic effect, and a decrease in myocardial oxygen demands. |
| 16 | lansoprazole | 0.911 | A proton pump inhibitor (PPI) and a potent inhibitor of gastric acidity. |
| 17 | nialamide | 0.911 | A non-selective, irreversible monoamine oxidase inhibitor of the hydrazine class that was used as an antidepressant. It was withdrawn by Pfizer several decades ago due to the risk of hepatotoxicity. |
| 18 | hydralazine | 0.909 | An antihypertensive with vasodilatory effects. |
| 19 | S-propranolol | 0.906 | The active enantiomer of propranolol, a $\beta$-adrenergic receptor antagonist. |
| 20 | nomifensine | 0.906 | A norepinephrine-dopamine reuptake inhibitor. |

TABLE 5A4

Drugs Identified Using Gene Expression Panels of Predictive
Biomarkers in Males (n = 17 probe sets/genes; 6 increased and 11
decreased were present in HG-U133A array used by CMAP).
Panel of genes increased in expression: FCGR1A, GAP43, MAPT,
KIDINS220, AIMP2, RGS10
Panel of genes decreased in expression: NDUFA5, SEC24A, PSMA4, UBE2L3,
NPC2, BST2, TGFB1, TRIM38, ZNF345, IGF1, VEGFA

| rank | CMAP name | score | Description |
|---|---|---|---|
| 1 | natamycin | 1 | Ophthalmic antifungal suspension. |
| 2 | mepenzolate bromide | 0.9 | An oral, quaternary anticholinergic gastrointestinal agent used for adjunctive treatment of peptic ulcer disease. |
| 3 | valinomycin | 0.896 | A natural antibiotic derived from *Streptomyces*. It also binds potassium ions and facilitates their transfer across lipid bilayers. |
| 4 | aminohippuric acid | 0.881 | Non-toxic diagnostic tool to measure effective renal plasma flow. |
| 5 | dexpropranolol | 0.859 | A non-selective β-adrenergic blocker. Studies have shown propranolol reduces cognitive deficits and amyloid/tau pathology in AD simulated mice. |
| 6 | valproic acid | 0.851 | A histone deacetylase inhibitor commonly used as an anticonvulsant and antimanic agent. Studies show valproic acid enhances memory and cognition in mice models. |
| 7 | dicloxacillin | 0.85 | A penicillin antibiotic. |
| 8 | pronetalol | 0.837 | An early non-selective β-blocker candidate that was not used clinically as it formed a carcinogenic metabolite in mice. |
| 9 | iobenguane | 0.837 | A guanidine analog with specific affinity for tissues of the sympathetic nervous system. The radiolabeled forms are used as antineoplastic or radioactive imaging agents. May be useful for diagnosing AD or dementia with Lewey bodies. |
| 10 | todralazine | 0.829 | An antihypertensive agent with central and peripheral action. It has some CNS depressant effects as well. |
| 11 | torasemide | 0.827 | An anilinopyridine sulfonylurea belonging to the class of loop diuretics. |
| 12 | gallamine triethiodide | 0.824 | A non-depolarising muscle relaxant. It acts by combining with the cholinergic receptor sites in muscle and competitively blocking the transmitter action of acetylcholine. |
| 13 | sulconazole | 0.822 | An antifungal medication of the imidazole class. |
| 14 | chlormezanone | 0.82 | A non-benzodiazepine muscle relaxant. It was discontinued worldwide in 1996 due to rare but serious cases of toxic epidermal necrolysis. |
| 15 | amantadine | 0.818 | A primary amine that has both antiviral and dopaminergic activity and is used in the therapy of influenza A and management of Parkinson disease. |
| 16 | tubocurarine chloride | 0.818 | A neuromuscular blocker and active ingredient in curare; plant based alkaloid of Menispermaceae. |
| 17 | protriptyline | 0.805 | A tricyclic antidepressant. |
| 18 | indometacin | 0.8 | A nonsteroidal anti-inflammatory drug (NSAID). |
| 19 | thioguanosine | 0.799 | A thio analogue of the naturally occurring purine base guanine used to treat acute myeloid leukemia, acute lymphocytic leukemia, and chronic myeloid leukemia. |
| 20 | adenosine phosphate | 0.797 | A nucleotide that is found in RNA. |

TABLE 5A5

Drugs Identified Using Gene Expression Panels of Predictive Biomarkers
in Females (n = 13 probe sets/genes; 1 increased and 4 decreased were present
in HG-U133A array used by CMAP).
Panel of genes increased in expression: CHAT
Panel of genes decreased in expression: GUSB, CD40, SERTAD3, TBRG4

| rank | CMAP name | score | Description |
|---|---|---|---|
| 1 | benserazide | 1 | Peripherally acting aromatic L-amino acid decarboxylase or DOPA decarboxylase inhibitor, which is unable to cross the blood-brain barrier. Recent studies by Jonkers et al. and Shen et al. revealed that benserazide can enter the brain and affect levodopa metabolism. |

TABLE 5A5-continued

Drugs Identified Using Gene Expression Panels of Predictive Biomarkers
in Females (n = 13 probe sets/genes; 1 increased and 4 decreased were present
in HG-U133A array used by CMAP).
Panel of genes increased in expression: CHAT
Panel of genes decreased in expression: GUSB, CD40, SERTAD3, TBRG4

| rank | CMAP name | score | Description |
|---|---|---|---|
| 2 | TTNPB | 0.99 | Selective and highly potent retinoic acid analog with affinity for retinoic acid receptors (RAR) $\alpha$, $\beta$, and $\gamma$, which are nuclear transcription factors. Activation of RAR and RXR is known to impede the pathogenesis of AD in mice by inhibiting accumulation of amyloids. |
| 3 | suxibuzone | 0.979 | Analgesic used for joint and muscular pain. |
| 4 | 15-delta prostaglandin J2 | 0.962 | Prostaglandin J derivative. It has a role as a metabolite, an electrophilic reagent and an insulin-sensitizing drug. Koma et al. found 15d-PGJ2-impaired memory retrieval significantly. Pereira et al. concluded therapeutic potential of targeting the J2 prostaglandin pathway to prevent/delay neurodegeneration associated with neuroinflammation |
| 5 | hydroquinine | 0.961 | Anti-arrhythmia agent and parasympatholytic. |
| 6 | rosiglitazone | 0.954 | An antidiabetic drug in the thiazolidinedione class. It works as an insulin sensitizer, by binding to the PPAR in fat cells and making the cells more responsive to insulin. Rosiglitazone reverses memory decline and hippocampal glucocorticoid receptor down-regulation in an Alzheimer's disease mouse model (Escribano 2009). In Phase 2 clinical trials for determining role in learning and memory in patients diagnosed with MCI. |
| 7 | colchicine | 0.942 | An anti-inflammatory which acts by inhibition of microtubule polymerization. Impairs memory function in a dose-dependent manner and is used as a model to induce Alzheimer's disease in rats. |
| 8 | 2,6-dimethylpiperidine | 0.942 | — |
| 9 | primaquine | 0.939 | An antimalarial agent that acts by interfering with the mitochondria of parasites. |
| 10 | 15-delta prostaglandin J2 | 0.931 | Prostaglandin J derivative. It has a role as a metabolite, an electrophilic reagent and an insulin-sensitizing drug. Koma et al. found 15d-PGJ2-impaired memory retrieval significantly. Pereira et al. concluded therapeutic potential of targeting the J2 prostaglandin pathway to prevent/delay neurodegeneration associated with neuroinflammation |
| 11 | meropenem | 0.925 | Carbapenem antibiotic. |
| 12 | anabasine | 0.924 | A nicotine analog that is an alkaloid. Has demonstrated improvement in memory and attention in rats. |
| 13 | cyclizine | 0.919 | A piperazine-derivative antihistamine used as an antivertigo/antiemetic agent. |
| 14 | norcyclobenzaprine | 0.919 | A metabolite of cyclobenzaprine (a muscle relaxant). |
| 15 | naftopidil | 0.918 | An $\alpha$1-adrenergic receptor antagonist. |
| 16 | BAS-012416453 | 0.914 | — |
| 17 | AG-012559 | 0.912 | — |
| 18 | terbutaline | 0.91 | A $\beta$2 adrenergic receptor agonist. |
| 19 | clomipramine | 0.908 | A tricyclic antidepressant used in the therapy of obsessive-compulsive disorder. Associated with diminished metamemory and impaired priming and working memory. |
| 20 | methyldopa | 0.904 | An antihypertensive that is a competitive inhibitor of the enzyme DOPA decarboxylase which converts L-DOPA into dopamine. Has been associated with verbal memory impairment. |

Table 5B. Drug Repurposing Using L1000 Characteristic
Direction Signature Search Engine.

TABLE 5B1

Drugs Identified Using Gene Expression Panels of Top Biomarkers CFG ≥
12 (n = 18 unique genes; 8 increased and 10 decreased).
Panel of genes increased in expression: MAPT, GFAP, TREM2, ARSB,
IGF1, THRA, NPTX2
BACE1
Panel of genes decreased in expression: GSK3B, NPC2, PTGS2, PSEN1,
CTSS, GSTM3, UBE2I, GUSB, APOE, TGFB1

| Rank | Score | Drug | Description |
|---|---|---|---|
| 1 | 0.2778 | BRD-K03371390 | |
| 2 | 0.2778 | NCGC00185923-01 | |
| 3 | 0.2222 | BENZANTHRONE | Dye that binds to amyloid fibrils. |
| 4 | 0.2222 | SQ 22536 | Adenylyl cyclase inhibitor. |
| 5 | 0.2222 | ICARIIN | Prenylated flavanol glycoside from Epimedium sagittatum. Jin et al. 2014 has found that Icariin significantly improved learning and memory of transgenic mice models of AD via stimulation of the NO/cGMP pathway. Sheng et al. 2017 concluded that Icariin improves synaptic plasticity, and therefore learning and memory, in rat models of AD via the BDNF/TrkB/Akt pathway. |
| 6 | 0.2222 | YM 90709 | IL-5 receptor antagonist. |
| 7 | 0.2222 | QUIPAZINE MALEATE | Binds to serotonin receptors, particularly to 5HT2A and 5HT3. |
| 8 | 0.2222 | Cisapride | Serotonin 5-HT$_4$ receptor agonist. Galeotti et al. 1997 revealed that cisapride prevented dicylomine-induced amnesia in mice suggesting it plays an important role in modulation of memory processes. No further studies have been published. |
| 9 | 0.2222 | LEUCINE ENKEPHALIN | Enkephalin. Meilandt et al. 2008 found that enkephalin elevations may contribute to cognitive impairments in mice models of AD. |
| 10 | 0.2222 | MLN4924 | An ubiquitin-like protein with roles relevant to cellular processes important for cancer cell survival. |
| 11 | 0.2222 | 2-(trifluoromethyl)-10H-phenothiazine | |
| 12 | 0.2222 | brucine | An alkaloid antagonist at glycine receptors and paralyzes inhibitory neurons. It is a low potency M$_1$ positive allosteric modulator. There is high expression of M$_1$ in areas of the brain responsible for learning, cognition, and memory. |
| 13 | 0.2222 | Clodronate | A bisphosphonate that affects calcium metabolism and inhibits bone resorption. Park et al. 2017 concluded that in mice studies clodronate diminishes brain perivascular macrophages which prohibits amyloid-beta from damaging brain blood vessels. However, this effect is limited to a few weeks. |
| 14 | 0.1667 | Vincristine sulfate | An alkaloid that irreversibly binds to microtubules and spindle proteins. It is an antineoplastic agent used to treat a variety of cancers. |
| 15 | 0.1667 | AZ 10417808 | A selective caspase-3 inhibitor. |
| 16 | 0.1667 | CCCP | A proton ionophore. |
| 17 | 0.1667 | Flurofamide | A potent inhibitor of bacterial urease. |
| 18 | 0.1667 | Chelidonine (+) | An inhibitor of tubulin polymerization inducing a G2/M mitotic arrest. Dickey et al. 2006 reported that chelidonine reduced tau levels in vitro. |
| 19 | 0.1667 | | Commonly known as turmeric. It is a scavenger of oxygen species and inhibits lipid peroxidation as well as peroxide-induced DNA damage. Small et al. 2018 found that daily oral curcumin may lead to improved memory and attention in non-demented adults. Zhang et al. 2006 concluded that curcumin may enhance amyloid-beta uptake by macrophages in AD patients. Lin et al. 2008 reported that curcumin significantly blocks the formative effect of iron on neurofibrillary tangles in vitro. |

TABLE 5B1-continued

Drugs Identified Using Gene Expression Panels of Top Biomarkers CFG ≥
12 (n = 18 unique genes; 8 increased and 10 decreased).
Panel of genes increased in expression: MAPT, GFAP, TREM2, ARSB,
IGF1, THRA, NPTX2
BACE1
Panel of genes decreased in expression: GSK3B, NPC2, PTGS2, PSEN1,
CTSS, GSTM3, UBE2I, GUSB, APOE, TGFB1

| Rank | Score | Drug | Description |
|------|-------|------|-------------|
| 20 | 0.1667 | rizatriptan | Several studies have revealed anti-Alzheimer's effects in mice and rat models (Lim et al. 2001, Garcia-Alloza et al. 2007, Ahmed et al. 2011). A selective agonist of serotonin type 1B and 1D receptors. |

TABLE 5B2

Drugs Identified Using Gene Expression Panels of Top Biomarkers
CFG ≥ 10 (n = 112 unique genes; 53 increased and 59 decreased).
Panel of genes increased in expression: LMNA, FOXO3, CCND2, PMP22, BCAM,
ELOVL6, HFE, NAV2, SLC1A7, FTL, MAPT, GFAP, LDLR, C4A, SNCA, THRA,
TREM2, CSF1, IL1A, NRP2, GAP43, RCOR1, KIDINS220, CHAT,
NPTX2, PON2, ANK1, IGF1, IGHG1, KLF3, FXYD1, COX6A1
AXL, PER1, SH3RF2, PPP2R2B, CLDN10, RGS10, FCGR1A, ITGB5,
APOA1, WASF2, ZBTB16, OPHN1, ARG2, SHC3, TSPAN5, NLGN3,
ARSB, AIMP2, CSNK1A1, RPL38, BACE1
Panel of genes decreased in expression: GSK3B, APOE, HELZ, VEGFA,
HSPA5, ZFP36L1
TGFB1, NDUFA5, ITPKB, DKK1, NOCT, SLC44A1, RHEB, NKTR, PGK1,
SALL3, WDR45, CSF1R
ICAM1, ABCA7, INPP5D, GAPDH, DUSP6, SREBF1, UQCRC1, TPK1,
GSTM3, MICA, DLD, PSMA4
PSEN1, GUSB, BST2, CD36, NDUFS3, CTSS, MPEG1, TYROBP, B2M,
RNASET2, FNBP1, USPL1
CEP350, FDPS, MTF2, RAB7A, PTGS2, NPC2, LYST, SERTAD3, SEC24A,
HSBP1, SNRK, TRIM38
NUP214, UBE2I, ASPHD2, UBE2L3, ZC3HAV1.

| Rank | Score | Drug | Description |
|------|-------|------|-------------|
| 1 | 0.1038 | Proparacaine hydrochloride | Local anesthetic |
| 2 | 0.0943 | BRD-K00944562 | |
| 3 | 0.0943 | BRD-A80151636 | |
| 4 | 0.0943 | BRD-K05361803 | |
| 5 | 0.0943 | BRD-K82137294 | |
| 6 | 0.0943 | BRD-K34206396 | |
| 7 | 0.0943 | Pioglitazone | A drug of the thiazolidinedione (TZD) class with hypoglycemic (antihyperglycemic, antidiabetic) action, used to treat diabetes |
| 8 | 0.0849 | TENOXICAM | NSAID |
| 9 | 0.0849 | AC-1133 | |
| 10 | 0.0849 | Vincamine | An antihypertensive with vasodilatory effects. |
| 11 | 0.0755 | 5-nonyloxytryptamine | An 5-HT1B selective agonist. |
| 12 | 0.0755 | CINANSERIN | A serotonin antagonist. |
| 13 | 0.0755 | Phenoxazine | A dye which consists of an oxazine fused to two benzene rings. |
| 14 | 0.0755 | elesclomol | An inducer of heat shock protein 70 that activates natural killer cell-mediated tumor killing. |
| 15 | 0.0755 | curcumin | A scavenger of oxygen species and inhibits lipid peroxidation as well as peroxide-induced DNA damage. |
| 16 | 0.0755 | TOLAZAMIDE | A sulfonylurea with hypoglycemic activity. |
| 17 | 0.0755 | Gly-Gly-delta-N-(phosphonacetyl)-L-ornithine | |
| 18 | 0.0755 | bestatin | A metalloprotease inhibitor selective for aminopeptidase. |
| 19 | 0.0755 | levofloxacin | A fluoroquinolone antibiotic. |
| 20 | 0.0755 | valaciclovir | A DNA polymerase inhibitor. |

TABLE 5B3

Drugs Identified Using Gene Expression Panels of Predictive Biomarkers in
All (n = 31 genes; 14 increased and 17 decreased).
Panel of genes increased in expression: FCGR1A, GAP43, MAPT, HFE, RGS10,
CALHM1 ARSB, LOC101928760, LOC101928123, RAB7A, TYMSOS,
LOC100499194, ITPKB, LOC105371414
Panel of genes decreased in expression: NDUFA5, SEC24A, PSMA4, UBE2L3,
NPC2, GUSB, TGFB1, TRIM38, CD40, ZNF345, IGF1, LOC101927027,
MIS18BP1, RHEB, CARD11, NKTR, MS4A14

| Rank | Score | Drug | Description |
|---|---|---|---|
| 1 | 0.1818 | CUNEATIN METHYL ETHER | |
| 2 | 0.1818 | GR 159897 | A potent and selective NK$_2$ receptor antagonist. |
| 3 | 0.1818 | Compound 58 | |
| 4 | 0.1818 | ROLIPRAM | A selective phosphodiesterase-4 inhibitor. |
| 5 | 0.1818 | BRD-K01089529 | |
| 6 | 0.1818 | BRD-K15888437 | |
| 7 | 0.1818 | BRD-K17025677 | |
| 8 | 0.1818 | 7618107 | |
| 9 | 0.1818 | BL-074 | |
| 10 | 0.1818 | BRD-A79981887 | |
| 11 | 0.1818 | BRD-A32164164 | |
| 12 | 0.1818 | BRD-K02562327 | |
| 13 | 0.1818 | BRD-K74767048 | |
| 14 | 0.1364 | vorinostat | A histone deacetylase inhibitor. |
| 15 | 0.1364 | curcumin | A scavenger of oxygen species and inhibits lipid peroxidation as well as peroxide-induced DNA damage. |
| 16 | 0.1364 | trichostatin A | A histone deacetylase inhibitor. |
| 17 | 0.1364 | JW-7-24-1 | |
| 18 | 0.1364 | geldanamycin | A benzoquinone antineoplastic antibiotic isolated from the bacterium *Streptomyces hygroscopicus*. |
| 19 | 0.1364 | MAPP, L-erythro | |
| 20 | 0.1364 | Piperacetazine | An antipsychotic prodrug. |

TABLE 5B4

Drugs Identified Using Gene Expression Panels of Predictive
Biomarkers in Males (n = 34 genes; 15 increased and 19 decreased).
Panel of genes increased in expression: FCGR1A, GAP43, MAPT,
KIDINS220, AIMP2, RGS10, PER1, RAB7A, KLF3, CALHM1, BACE1,
ARSB, LOC101928123, LOC100499194, ITPKB
Panel of genes decreased in expression: NDUFA5, SEC24A, PSMA4,
UBE2L3, NPC2, BST2, TGFB1, TRIM38, ZNF345, IGF1, VEGFA,
LOC101927027, MIS18BP1, RHEB CARD11, NKTR, MS4A14,
B2M, EPB42

| Rank | Score | Drug | Description |
|---|---|---|---|
| 1 | 0.1786 | Triamcinolone | A synthetic glucocorticorsteroid. |
| 2 | 0.1786 | N20C hydrochloride | Non-competitive NMDA receptor open-channel blocker. |
| 3 | 0.1786 | manumycin A | An antibiotic that acts as a potent and selective farnesyltransferase inhibitor. |
| 4 | 0.1786 | NCGC00183397-01 | |
| 5 | 0.1786 | BRD-K71917235 | |
| 6 | 0.1786 | BRD-A32164164 | |
| 7 | 0.1429 | L-690,330 | |
| 8 | 0.1429 | PERHEXILINE MALEATE | A carnitine CPT1 and CPT2 inhibitor. |
| 9 | 0.1429 | Clobetasol propionate | A corticosteroid. |
| 10 | 0.1429 | GR 159897 | A NK2 receptor antagonist. |
| 11 | 0.1429 | NOBILETIN | An O-methylated flavone that has the activity to rescue bulbectomy-induced memory impairment. |
| 12 | 0.1429 | ENDECAPHYLLIN X | A glucose tetra-(3-nitropropanoate) ester. |
| 13 | 0.1429 | Flurandrenolide | A corticosteroid. |
| 14 | 0.1429 | SDZ WAG 994 | A potent and selective A1 adenosine receptor agonist. |
| 15 | 0.1429 | Timolol maleate salt | A non-selective beta-adrenergic antagonist. |

TABLE 5B4-continued

Drugs Identified Using Gene Expression Panels of Predictive
Biomarkers in Males (n = 34 genes; 15 increased and 19 decreased).
Panel of genes increased in expression: FCGR1A, GAP43, MAPT,
KIDINS220, AIMP2, RGS10, PER1, RAB7A, KLF3, CALHM1, BACE1,
ARSB, LOC101928123, LOC100499194, ITPKB
Panel of genes decreased in expression: NDUFA5, SEC24A, PSMA4,
UBE2L3, NPC2, BST2, TGFB1, TRIM38, ZNF345, IGF1, VEGFA,
LOC101927027, MIS18BP1, RHEB CARD11, NKTR, MS4A14,
B2M, EPB42

| Rank | Score | Drug | Description |
|---|---|---|---|
| 16 | 0.1429 | RHAPONTIN | A crystalline glucoside found in rhubarb. |
| 17 | 0.1429 | 16759925 | |
| 18 | 0.1429 | simvastatin | A HMG-CoA reductase inhibitor. |
| 19 | 0.1429 | 2541665-P2 | |
| 20 | 0.1429 | Compound 58 | |

TABLE 5B5

Drugs Identified Using Gene Expression Panels of Predictive Biomarkers
in Females (n = 12 genes; 6 increased and 6 decreased).
Panel of genes increased in expression: DEFB104B, LINC01398,
CHAT, RTCB, LOC105371414, PER1
Panel of genes decreased in expression: ITPKB, GUSB, CD40,
SERTAD3, TBRG4, MS4A14

| Rank | Score | Drug | Description |
|---|---|---|---|
| 1 | 0.2857 | Fluticasone propionate | A synthetic trifluorinated glucocorticoid receptor agonist. |
| 2 | 0.2857 | Anisomycin | An antibiotic isolated from various *Streptomyces* species. |

TABLE 5B5-continued

Drugs Identified Using Gene Expression Panels of Predictive Biomarkers
in Females (n = 12 genes; 6 increased and 6 decreased).
Panel of genes increased in expression: DEFB104B, LINC01398,
CHAT, RTCB, LOC105371414, PER1
Panel of genes decreased in expression: ITPKB, GUSB, CD40,
SERTAD3, TBRG4, MS4A14

| Rank | Score | Drug | Description |
|---|---|---|---|
| 3 | 0.2857 | DIGOXIN | A cardiotonic glycoside obtained mainly from *Digitalis lanata*. |
| 4 | 0.2857 | NICARDIPINE HYDROCHLORIDE | A calcium channel blockader with vasodilatory properties. |
| 5 | 0.2857 | BRD-K06593056 | |
| 6 | 0.2857 | Inhibitor BEC hydrochloride | A competitive inhibitor of arginases I and II that causes NO-dependent smooth muscle relaxation. |
| 7 | 0.2857 | Emetine Dihydrochloride Hydrate (74) | A protein synthesis inhibitor derived from ipecac root. |
| 8 | 0.2857 | Importazole | A nuclear transport receptor importin-beta inhibitor. |
| 9 | 0.2857 | Salermide | An inhibitor of SIRT1 and SIRT2 causing tumor-specific apoptotic cell death. |
| 10 | 0.2857 | BRD-K72264770 | |
| 11 | 0.2857 | dibenzyline | An alpha-adrenergic antagonist. |
| 12 | 0.2857 | CGP-60474 | A cyclin-dependent kinase inhibitor. |
| 13 | 0.2857 | HG-5-88-01 | |
| 14 | 0.2857 | Scopolamin-N-oxide hydrobromide | An antagonist of the muscarinic acetylcholine receptor. |
| 15 | 0.2857 | REV-5901 | An antagonist of cysteinyl-leukotriene receptors. |
| 16 | 0.2857 | TRANS-7-HYDROXY-PIPAT | A dopamine D3 receptor ligand. |
| 17 | 0.2857 | Biotin | Vitamin B7. |
| 18 | 0.2857 | NNC 711 | An anticonvulsant that works as a selective inhibitor of GABA uptake by GAT-1. |
| 19 | 0.2857 | L-693,403 maleate | σ ligand selectivity over the dopamine D2 receptor. |
| 20 | 0.2857 | W-7 hydrochloride | Calmodulin antagonist. |

Table 5C. Drug Repurposing using Crowd Extracted Expression of Differential Signatures (CREED)

TABLE 5C1

Drugs Identified Using Gene Expression Signature of Top Biomarkers
CFG ≥ 12 (n = 18 unique genes; 8 increased and 10 decreased).

| Rank | Name | Signed Jaccard Index | Description |
|---|---|---|---|
| 1 | Lorazepam | 0.00727 | A benzodiazepine. |
| 2 | Finasteride | 0.00656 | A 5-alpha reductase inhibitor. |
| 3 | Bromhexine | 0.00649 | An expectorant/mucolytic agent. |
| 4 | Ethinylestradiol | 0.00641 | A semisynthetic estrogen. |
| 5 | Dicumarol | 0.00639 | Isolated from molding sweet-clover hay, with anticoagulant and vitamin K depletion activities. |
| 6 | Letrozole | 0.00613 | A nonsteroidal inhibitor of aromatase. |
| 7 | Promazine | 0.0061 | A phenothiazine derivative with antipsychotic and antiemetic properties. |
| 8 | Diisopropyl Fluorophosphate | 0.00598 | An irreversible cholinesterase inhibitor. |
| 9 | Rapamycin | 0.00568 | A mTOR Inhibitor. |
| 10 | Doxorubicin | 0.00549 | A topoisomerase inhibitor. |
| 11 | Artemisinin | 0.00542 | A sesquiterpene lactone obtained from *Artemisia annua*, which has been recently found to have potent activity against many forms of malarial organisms. |
| 12 | Colchicine | 0.0054 | Microtubule inhibitor. |
| 13 | Mifepristone | 0.00526 | Progestin antagonist. |
| 14 | Zopiclone | 0.00526 | A central nervous system depressant and a sedative. |
| 15 | Amlodipine | 0.00526 | Calcium channel blocker. |
| 16 | Busulfan | 0.00524 | An alkylating agent used in the treatment of CML. |
| 17 | Rosiglitazone | 0.00524 | A selective agonist for PPAR GAMMA. |
| 18 | Norethindrone | 0.00523 | A synthetic progestin. |
| 19 | Letrozole | 0.00521 | A nonsteroidal inhibitor of aromatase. |
| 20 | Omeprazole | 0.00517 | Proton pump inhibitor. |

TABLE 5C2

Drugs Identified Using Gene Expression Signature of Top
Biomarkers CFG ≥ 10 (n = 112 unique genes; 68 increased and 64 decreased).

| Rank | Drug | Signed Jaccard Index | Description |
|---|---|---|---|
| 1 | Hydralazine | 0.01735 | An antihypertensive. |
| 2 | Rofecoxib | 0.0135 | NSAID. |
| 3 | Ethylene Glycol | 0.0134 | Dihydroxy alcohol. |
| 4 | Doxycycline | 0.01339 | A tetracycline antibiotic. |
| 5 | Levamisole | 0.0131 | An anthelmintic drug that has been tried as an adjuvant to chemotherapy. |
| 6 | Suxamethonium Chloride | 0.01301 | A depolarizing skeletal muscle relaxant. |
| 7 | Tiapride | 0.013 | A D2 and D3 dopamine receptor antagonist. |
| 8 | Bupropion | 0.01295 | An antidepressant of the aminoketone class and a non-nicotine aid to smoking cessation. |
| 9 | Promethazine | 0.01295 | A first generation antihistamine that is used an antiemetic. |
| 10 | Pyrazinamide | 0.01278 | A synthetic pyrazinoic acid amide derivative with bactericidal properties against *Mycobacterium tuberculosis*. |

TABLE 5C2-continued

Drugs Identified Using Gene Expression Signature of Top
Biomarkers CFG ≥ 10 (n = 112 unique genes; 68 increased and 64 decreased).

| Rank | Drug | Signed Jaccard Index | Description |
|---|---|---|---|
| 11 | Antimycin A | 0.01277 | An antibacterial that blocks electron transport between coenzyme Q and cytochrome c. |
| 12 | Metoprolol | 0.01273 | Competitive beta-1 adrenergic receptor antagonist. |
| 13 | Catechol | 0.01271 | It has a role as a genotoxin, an allelochemical and a plant metabolite. |
| 14 | Azathioprine | 0.01264 | A purine analogue that is used as an immunosuppressive agent. |
| 15 | Gadopentetate Dimeglumine | 0.01262 | A gadolinium-based paramagnetic contrast agent. |
| 16 | Epirubicin | 0.01247 | An anthracycline topoisomerase inhibitor. |
| 17 | Propylene Glycol | 0.01246 | Used as an organic solvent. |
| 18 | Thiabendazole | 0.01239 | A broad spectrum antihelmintic agent. |
| 19 | Leflunomide | 0.01231 | An immunomodulatory agent. |
| 20 | Imatinib | 0.01231 | Tyrosine kinase receptor inhibitor. |

For the top biomarkers (see, Table 5), all the evidence from discovery (up to 6 points), prioritization (up to 12 points), testing (state, trait—up to 6 points each if significantly predicts in all subjects, 4 points if predicts by gender, 2 points if predicts in gender/diagnosis) were tabulated into a convergent functional evidence (CFE) score. The total score could be up to 30 points: 18 from the experimental data and 12 from literature data. The experimental data was weighed more than the literature data.

Example 1

In this example, biomarkers for short-term memory were determined.

Longitudinal studies were conducted in psychiatric disorder subjects, a population enriched in memory retention abnormalities. The subjects had blood gene expression data at multiple testing visits, and were phenotyped at each visit, including with Hopkins Verbal Learning Test (HVLT). Subject's electronic medical records were also available for long term follow-up of outcomes.

In Step 1 Discovery, blood gene expression biomarkers were identified that track memory using a powerful within-subject design in a cohort of subjects who displayed at least a 20% change in the retention measure between different visits (n=159 subjects, with 496 visits), normalized (Z-scored) across genders and various psychiatric diagnoses. In Step 2 Prioritization, a Convergent Functional Genomics approach was used to prioritize the candidate biomarkers in Step 1, using published literature evidence (genetic, gene expression and proteomic), from human and animal model studies, for involvement in AD. In Step 3 Testing, an independent cohort (n=127) from the one used for discovery was examined for whether the top biomarkers prioritized in Step 2 were predictive of memory retention measure (state), and of future positive neuropsychological testing for MCI, AD or other dementia (trait), using electronic medical records follow-up data of the study subjects (up to 12.81 years from initial visit).

Figure 2:
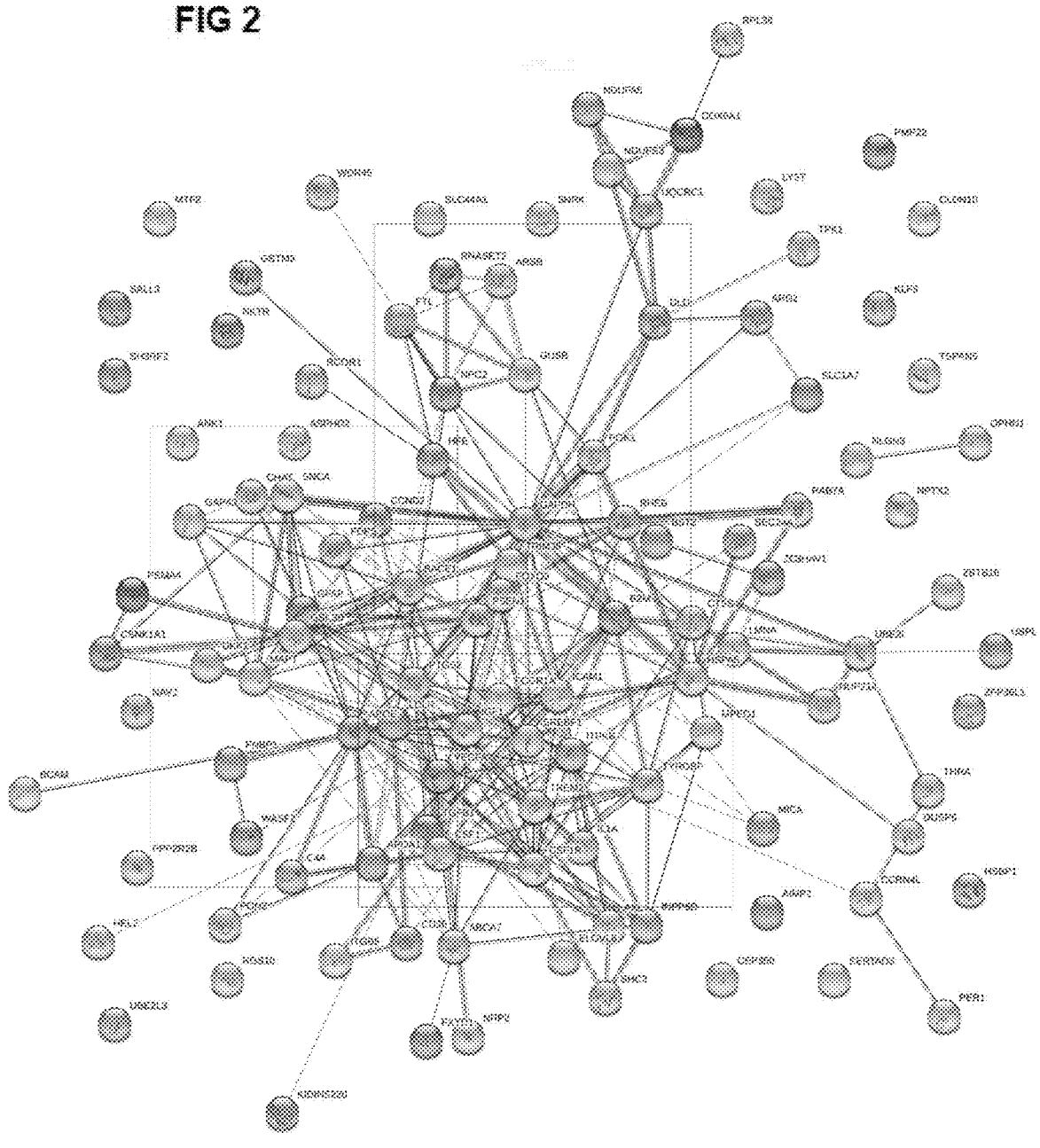
FIG. 2 is a schematic illustrating the interaction networks for top candidate biomarkers (n=111 top genes, 136 probe sets).

The top biological pathways where the candidate biomarkers map were related to LXR/RXR activation, neuroinflammation signaling atherosclerosis signaling, and amyloid processing (Table 2). Co-directionality of expression data provide new mechanistic insights that are consistent with a compensatory/scarring scenario for observed brain pathological changes. The STRING gene interaction analysis (FIG. 2) revealed at least 3 networks. Network 1 (red) includes TREM2, along with GUSB and RHEB; it may be involved in reactivity and inflammatory responses. Network 2 (green) includes MAPT (tau), along with PSEN1 and SNCA; it may be involved in activity and cellular trophicity. Network 3 (blue) includes APOE, along with TGFB1 and FOXO3; it may be involved in connectivity and synaptic integrity. GSK3B is at the overlap of Networks 2 and 3.

The top candidate biomarkers were prioritized for convergent evidence for involvement in AD (Table 5). They also had prior evidence of involvement in other psychiatric and related disorders, providing a molecular underpinning for the possible precursor effects of these disorders in AD.

Figure 3B:
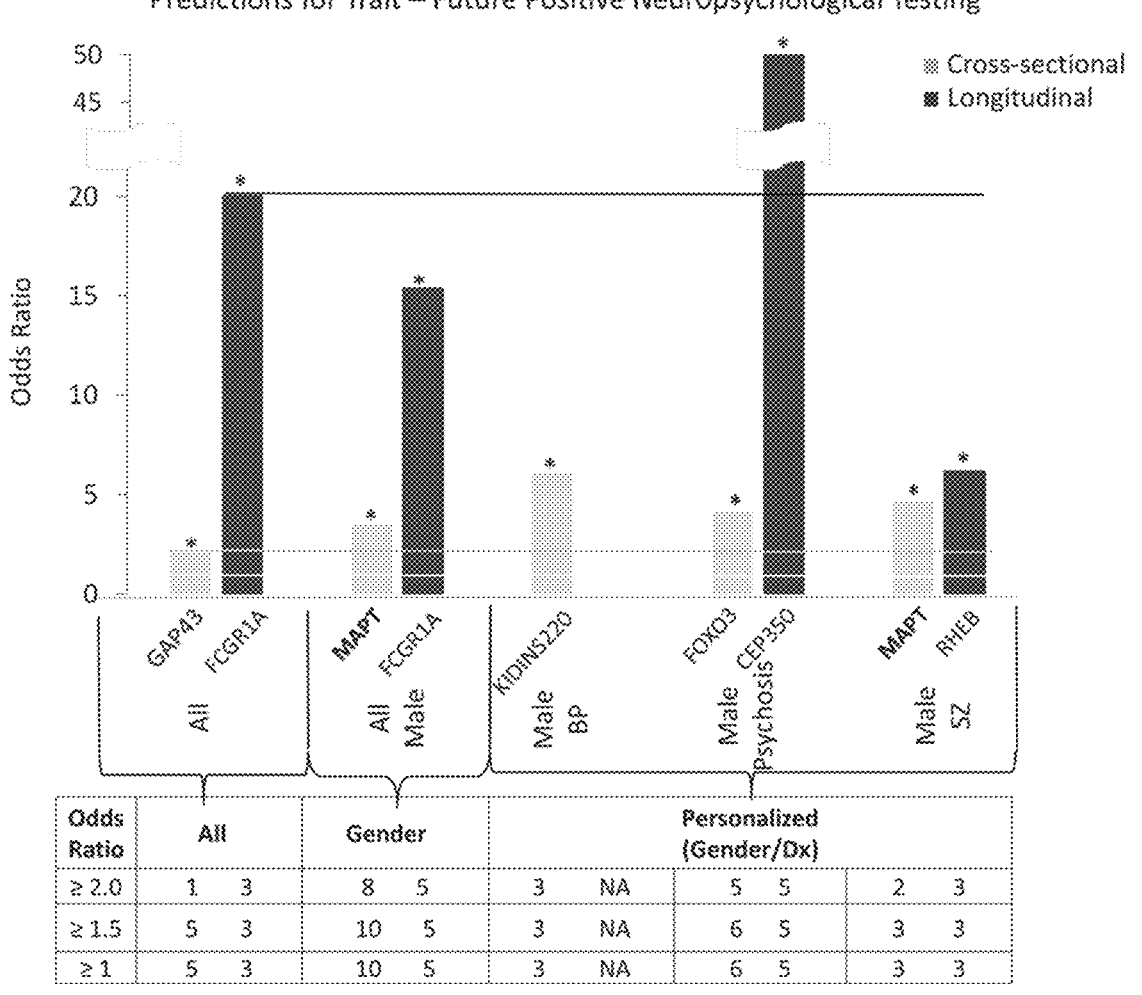

Gene expression biomarkers that were predictive in independent cohorts of memory state and of future neuropsychological testing positive for cognitive decline were successfully identified. Top predictive biomarkers for state were NKTR, ITPK, RGS10, PER1, and ARSB (FIG. 3A). The AUC ROCs ranged from over 0.7 for all subjects tested to over 0.8 personalized by gender, and over 0.9 personalized by gender and diagnosis. Top predictive biomarkers for trait were KLF3, CEP350, FOXO3, MAPT, and RHEB (FIG. 3B). The Cox Regression Odds Ratios ranged from over 2-fold for all subjects tested to over 4-fold personalized by gender and diagnosis.

Figure 4A:
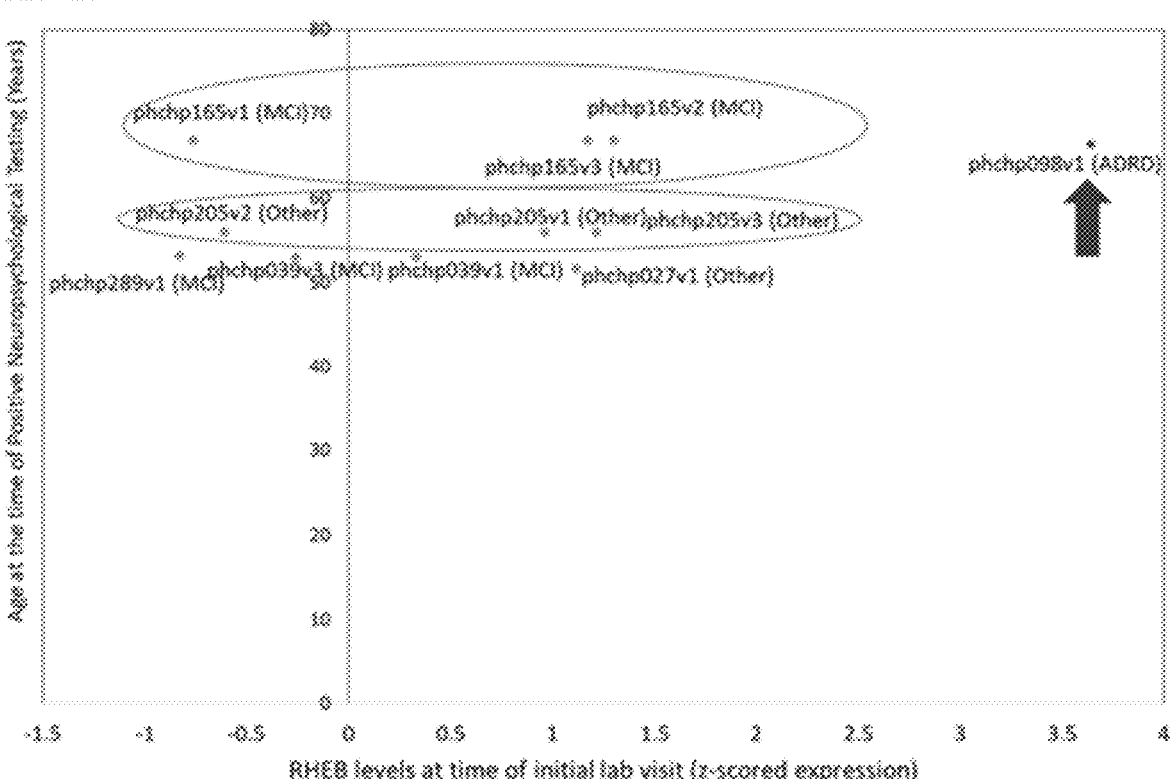
FIGS. 4A and 4B are graphs depicting RHEB as a possible personalized biomarker predictor for risk of future AD in Males with Schizophrenia. Subject Phchp098 was a male with schizophrenia (SZ) tested in 2009. He was first diagnosed with paranoid schizophrenia in 1977. In 2016, he was also diagnosed by neuropsychological testing with ADRD and impaired decision-making capacity. At that time, he was 66 years old. Subject was the only one so far with an ADRD diagnosis in the independent replication follow-up cohort. RHEB levels were Z-scored by gender and diagnosis. Subject Phchp098 had the highest levels of RHEB in testing from all the subjects with future neuropsychological testing (FIG. 4A), and in fact the highest level of RHEB from all the 111 subjects in that cohort (FIG. 4B).
Figure 4B:
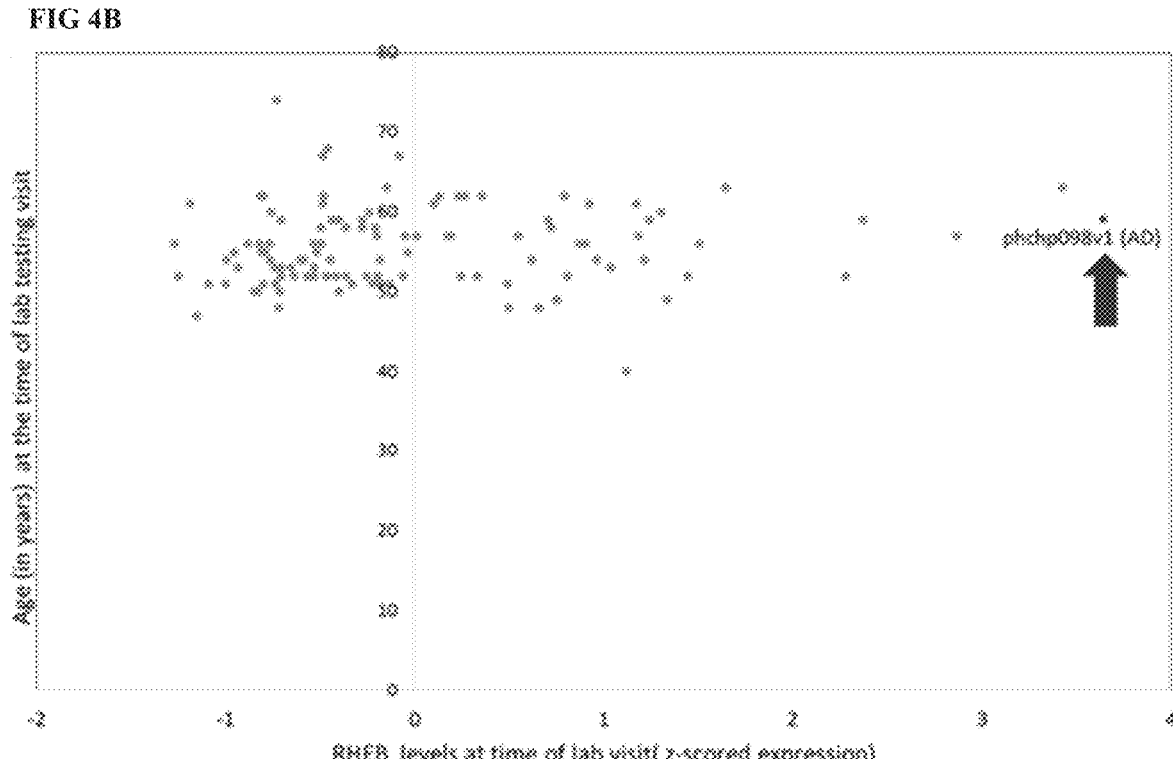

RHEB, which represents the best biomarker for male schizophrenia, was identified as a future Alzheimer Disorder Related Dementia predictor in males with schizophrenia (FIG. 4). Subject Phchp098 was a male with schizophrenia (SZ) initially tested in 2009. The subject was first diagnosed with paranoid schizophrenia in 1977. In 2016, he was also diagnosed by neuropsychological testing with ADRD and impaired decision-making capacity. At that time, he was 66 years old. Subject was the only subject so far with an ADRD diagnosis in the independent replication follow-up cohort. We tested RHEB, the best predictive biomarker for males with SZ (FIG. 2B). RHEB levels were Z-scored by gender and diagnosis. Subject Phchp098 had the highest levels of RHEB in the lab testing visit compared to all the subjects with future neuropsychological testing (FIG. 4A) and the highest level of RHEB from all the 111 subjects in that cohort (FIG. 4B).

Based on the studies and analyses, the biomarkers with the top overall convergent functional evidence (CFE) for relevance to memory and AD were NPC2, TGFB1, ARSB, GUSB, and KLF3, and then GSK3B, MAPT (tau), APOE, PSEN1, and TREM2. The fact that key genes for AD brain pathology came out of the unbiased whole-genome discovery was reassuring and served as de facto positive controls for the approach.

Figure 5:
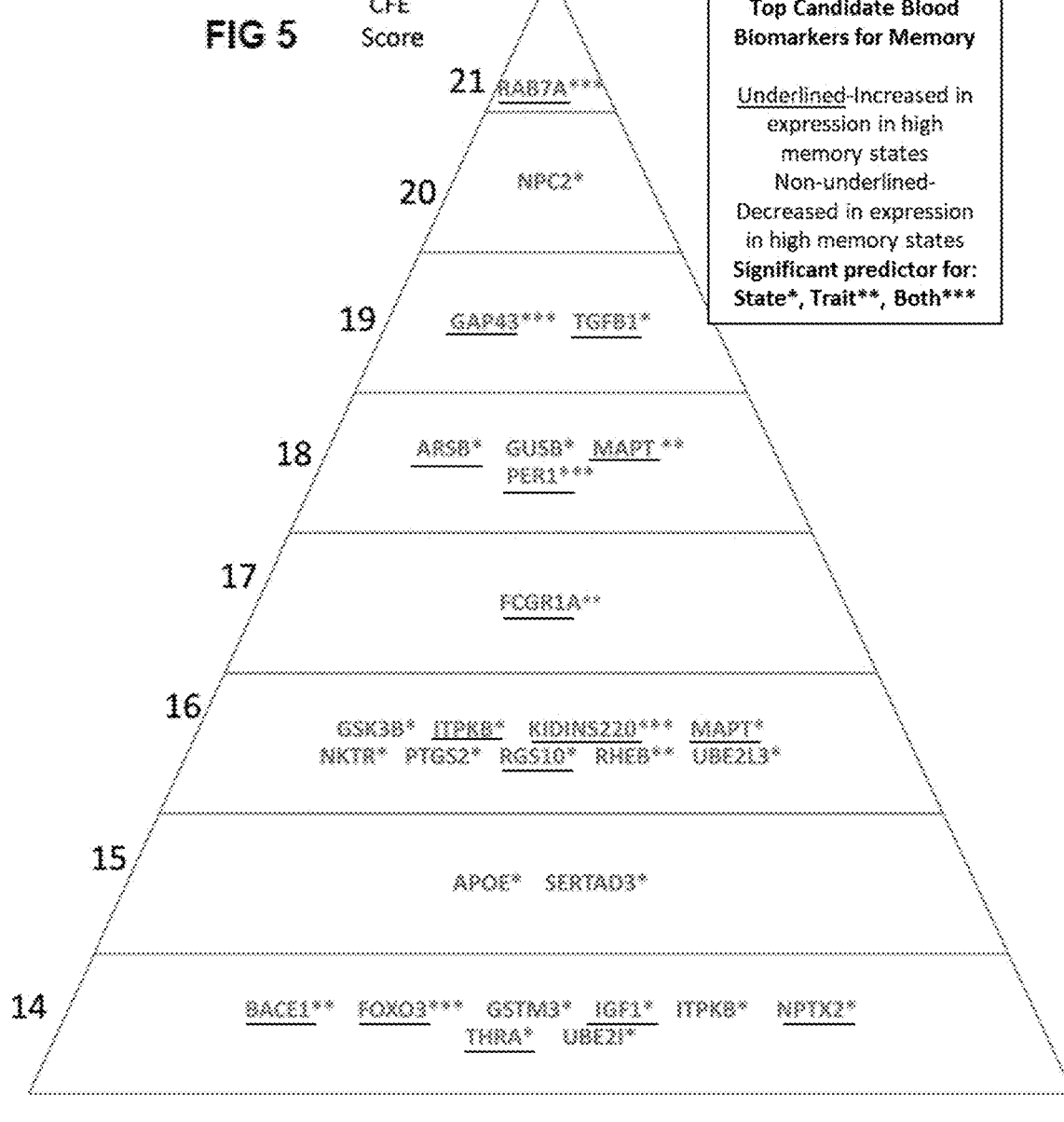
FIG. 5 is a schematic illustrating the pharmacogenomics of the top biomarkers modulated by existing drugs.

Some of the biomarkers are targets of existing drugs, such as lithium, antidepressants, and omega-3 fatty acids (FIG. 5; Table 3), of potential utility in patient stratification and pharmacogenomics approaches. Moreover, the top biomarkers gene expression signature, upon bioinformatics drug repurposing analyses, yielded new drug candidates (such as pioglitazone and levonorgestrel), and natural compounds (such as salsolidine, ginkgolide A and icariin). Thus, the signature can be used for targeted enrollment of patients in clinical trials for these compounds, which would increase the odds of success, and for objectively measuring response to treatment.

The methods described herein provide a novel approach for discovering biomarkers of relevance to Alzheimer's disease, as well as testing the biomarkers in independent cohorts. The results provide evidence for precision medicine, diagnostics and therapeutics. The methods can provide improved early diagnosis of risk and preventive treatment for memory disorders in general, and Alzheimer's disease in particular, that result in decreased quality and quantity of life, at a massive cost to individuals, families and society.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed:

1. A method for assessing a low memory state in a subject, the method comprising:
   a) obtaining RNA expression level data for a panel of biomarkers from a biological sample of a subject, wherein the panel of biomarkers comprises RAB7A, Niemann-Pick disease, type C (NPC2), transforming growth factor beta 1 (TGFB1), growth associated protein 43 (GAP43), arylsulfatase B (ARSB), period circadian clock 1 (PER1), glucuronidase, beta (GUSB), microtubule associated protein tau (MAPT), Fc fragment of IgG, high affinity Ia, receptor (CD64) (FCGR1A), ubiquitin conjugating enzyme E2L 3

(UBE2L3), natural killer cell triggering receptor (NKTR), Ras homolog enriched in brain (RHEB), prostaglandin-endoperoxide synthase 2 (PTGS2), regulator of G-protein signaling 10 (RGS10), inositol-trisphosphate 3-kinase B (ITPKB), kinase D-interacting substrate 220 kDa (KIDINS220), glycogen synthase kinase 3 beta (GSK3B), SERTA domain containing 3 (SERTAD3), apolipoprotein E (APOE), ubiquitin conjugating enzyme E2I (UBE2I), forkhead box O3 (FOXO3), thyroid hormone receptor, alpha (THRA), insulin-like growth factor 1 (IGF1), neuronal pentraxin II (NPTX2), glutathione S-transferase mu 3 (GSTM3), Beta-Secretase 1 (BACE1), presenilin 1 (PSEN1), glial fibrillary nacidic protein (GFAP), triggering receptor expressed on myeloid cells 2 (TREM2), nocturnin (NOCT), centrosomal protein 350 kDa (CEP350), protein phosphatase 2, regulatory subunit B (PPP2R2B), neuropilin 2 (NRP2), cathepsin S (CTSS), and vascular endothelial growth factor A (VEGFA);
   b) computing a score based on RNA level, protein level, DNA methylation, or a single nucleotide polymorphism, for the panel of biomarkers in the sample obtained from the subject;
   c) computing a reference score based on a reference expression levels for the biomarkers of the panel of biomarkers; and
   d) identifying in the sample obtained from the subject as compared to the reference score an increase in expression of RAB7A, TGFB1, GAP43, ARSB, PER1, MAPT, FCGR1A, RGS10, KIDINS220, FOXO3, THRA, IGF1, NPTX2, BACE1, GFAP, TREM2, PPP2R2B, NRP2 and VEGFA in the sample obtained from the subject and a decrease in expression of NPC2, GUSB, UBE2L3, NKTR, RHEB, PTGS2, GSK3B, SERTAD3, APOE, UBE2I, GSTM3, PSEN1, NOCT, CEP350, and CTSS in the sample obtained from the subject, wherein such changes in expression indicates a low memory state in the subject;
   e) wherein upon identifying a risk of low memory state in the subject, administering a treatment to the subject wherein the treatment reduces the difference between the score of the sample from the subject and the reference score and wherein a change in score upon administering the treatment indicates a response to the treatment; and
   wherein the treatment is a therapy selected from the group consisting of antidepressants, lithium, omega-3 fatty acids, pioglitazone, levonorgestrel, mesalazine, salsolidine, ginkgolide A, icariin, or a combination thereof.

2. The method of claim 1, further comprising measuring response to treatment by repeating the steps of the method of claim 1.

3. The method of claim 1 wherein the indication of a low memory state in the subject is an indication of risk of future Alzheimer Disease.

4. The method of claim 1, wherein the therapy is mesalazine.

* * * * *